(12) United States Patent
Miller et al.

(10) Patent No.: US 9,962,360 B2
(45) Date of Patent: May 8, 2018

(54) COMPOSITIONS AND METHODS FOR ENHANCING HAIR GROWTH, PROMOTING SKIN REGENERATION, AND WOUND HEALING

(71) Applicant: The Hospital for Sick Children, Toronto (CA)

(72) Inventors: Freda D. Miller, Toronto (CA); David R. Kaplan, Toronto (CA); Sibel Naska, Toronto (CA); Kristen Michelle Smith, San Clemente, CA (US); Maryline Paris, St Cloud (FR)

(73) Assignee: The Hospital for Sick Children, Toronto (CA)

( * ) Notice: Subject to any disclaimer, the term of this patent is extended or adjusted under 35 U.S.C. 154(b) by 0 days. days.

(21) Appl. No.: 15/513,877

(22) PCT Filed: Sep. 25, 2015

(86) PCT No.: PCT/CA2015/050966
§ 371 (c)(1),
(2) Date: Mar. 23, 2017

(87) PCT Pub. No.: WO2016/044951
PCT Pub. Date: Mar. 31, 2016

(65) Prior Publication Data
US 2017/0252316 A1  Sep. 7, 2017

Related U.S. Application Data

(60) Provisional application No. 62/055,195, filed on Sep. 25, 2014.

(51) Int. Cl.
| | | |
|---|---|---|
| *A61K 31/24* | (2006.01) | |
| *A61K 9/06* | (2006.01) | |
| *A61K 8/44* | (2006.01) | |
| *A61Q 7/00* | (2006.01) | |
| *A61K 9/00* | (2006.01) | |
| *A61K 45/06* | (2006.01) | |

(52) U.S. Cl.
CPC .............. *A61K 31/24* (2013.01); *A61K 8/445* (2013.01); *A61K 9/0014* (2013.01); *A61K 9/0053* (2013.01); *A61K 9/06* (2013.01); *A61K 45/06* (2013.01); *A61Q 7/00* (2013.01); *A61K 2800/74* (2013.01); *A61K 2800/92* (2013.01)

(58) Field of Classification Search
CPC ...... A61K 31/24; A61K 8/445; A61K 9/0014; A61K 9/0053; A61K 9/06; A61K 45/06; A61K 2800/74; A61K 2800/92; A61Q 7/00
USPC ......................................................... 514/171
See application file for complete search history.

(56) References Cited

U.S. PATENT DOCUMENTS

| | | |
|---|---|---|
| 7,666,907 B2 | 2/2010 | Wallace et al. |
| 2002/0058682 A1 | 5/2002 | Breton et al. |

FOREIGN PATENT DOCUMENTS

| | | |
|---|---|---|
| WO | WO-2012/018643 A2 | 2/2012 |
| WO | WO-2013/119984 A1 | 8/2013 |

OTHER PUBLICATIONS

International Search Report for International Patent Application No. PCT/CA2015/050966, dated Nov. 19, 2015 (6 pages).
Written Opinion for International Patent Application No. PCT/CA2015/050966, dated Nov. 19, 2015 (8 pages).
Aboul-Enein et al., "Esters of 1-(dimethylamino)-1-indan- and 1,2,3,4-tetrahydro-1-naphthalene methanols as antispasmodics, antiulcer drugs and local anaesthetics," Sci Pharm. 56(4):243-50 (1988).
Extended European Search Report for European Application No. 15845138.5, dated Feb. 13, 2018 (11 pages).
Kamiya et al., "Effects of trimebutine maleate on gastric motility in patients with gastric ulcer," J Gastroenterol. 33(6):823-7 (1998).
Martin-Garcia et al., "Delayed reaction urticaria due to trimebutine," Allergy. 59(7):789-90 (2004).
Tan et al., "Effects of trimebutine maleate on colonic motility through $Ca^{2+}$-activated K+ channels and L-type $Ca^{2}$ + channels," Arch Pharm Res. 34(6):979-85 (2011).

*Primary Examiner* — Yevgeny Valenrod
(74) *Attorney, Agent, or Firm* — Clark & Elbing LLP

(57) ABSTRACT

The invention relates to compositions and methods useful for enhancing hair growth and promoting skin regeneration. Particularly, the invention provides topical compositions including trimebutine, salts, or active metabolites thereof, for enhancing or inducing hair growth and promoting skin regeneration. Compositions comprising trimebutine or a pharmaceutically acceptable salt or active metabolite thereof and their use in the method of promoting hair growth or skin regeneration. Preferably trimebutine is trimebutine maleate or N-desmethyl trimebutine. Compositions are preferably in a form for topical administration, such as a gel.

14 Claims, 25 Drawing Sheets

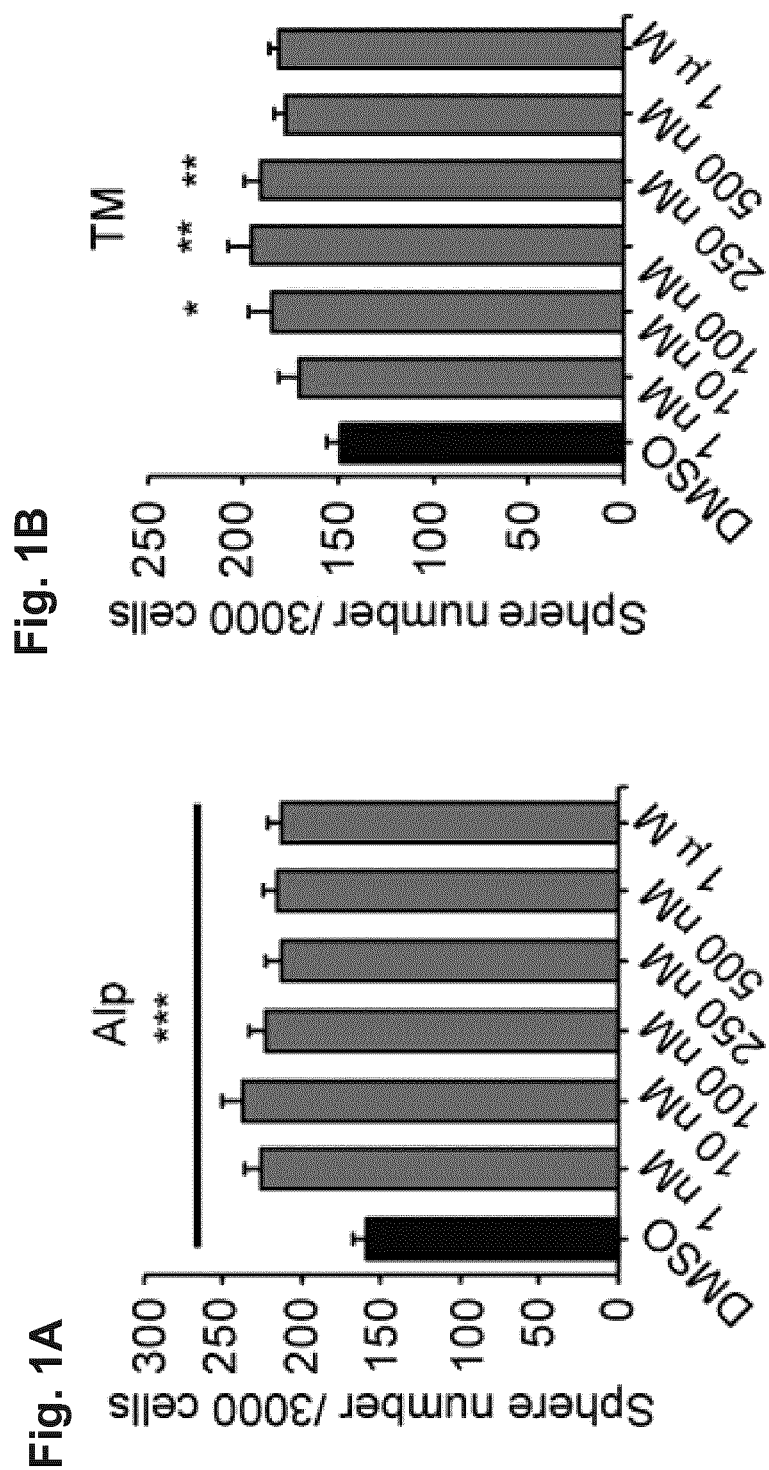

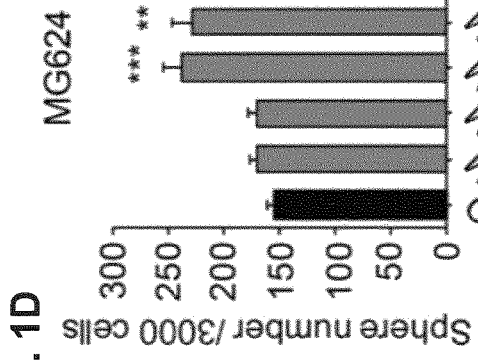
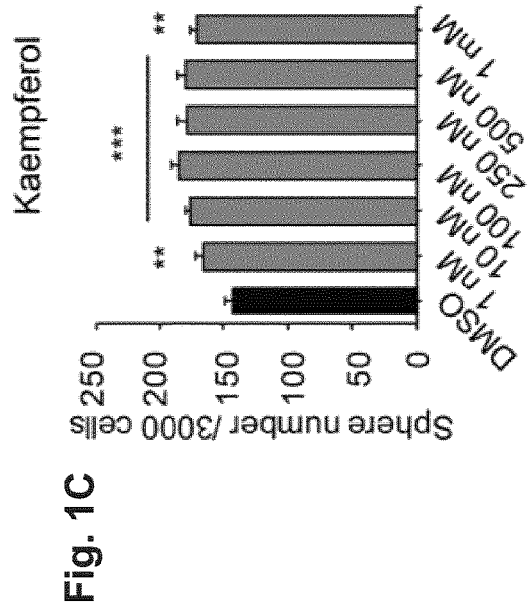
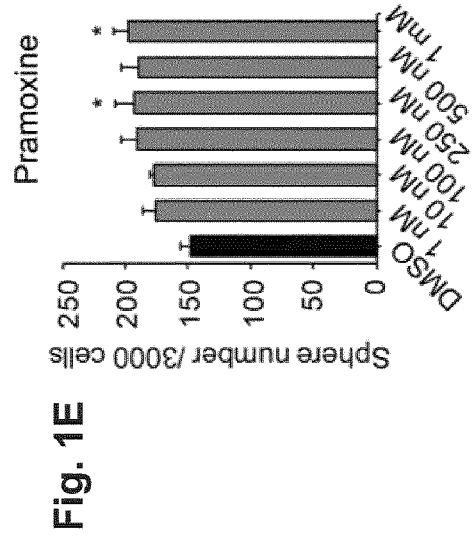

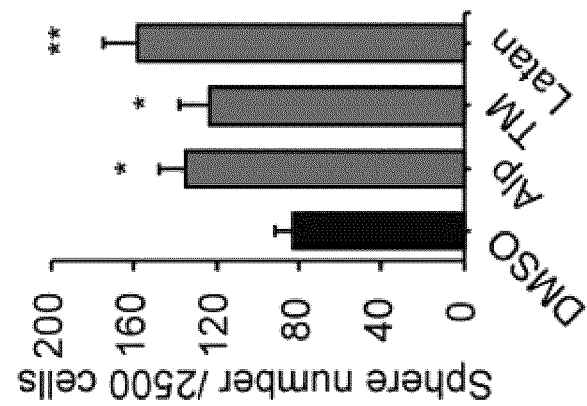
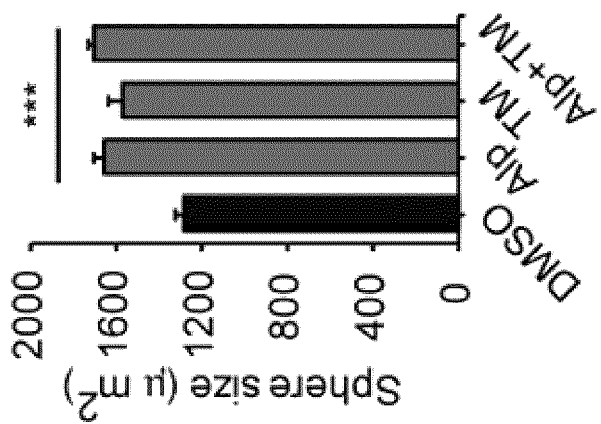
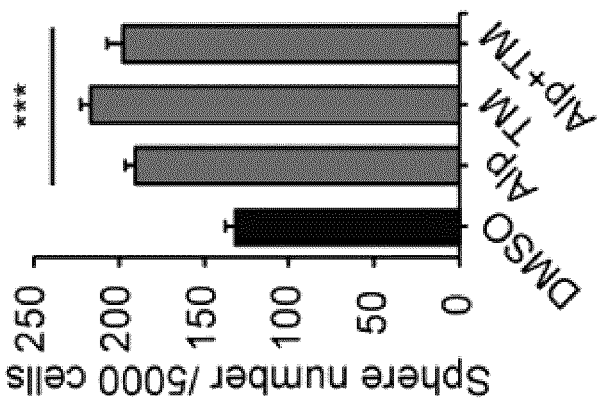

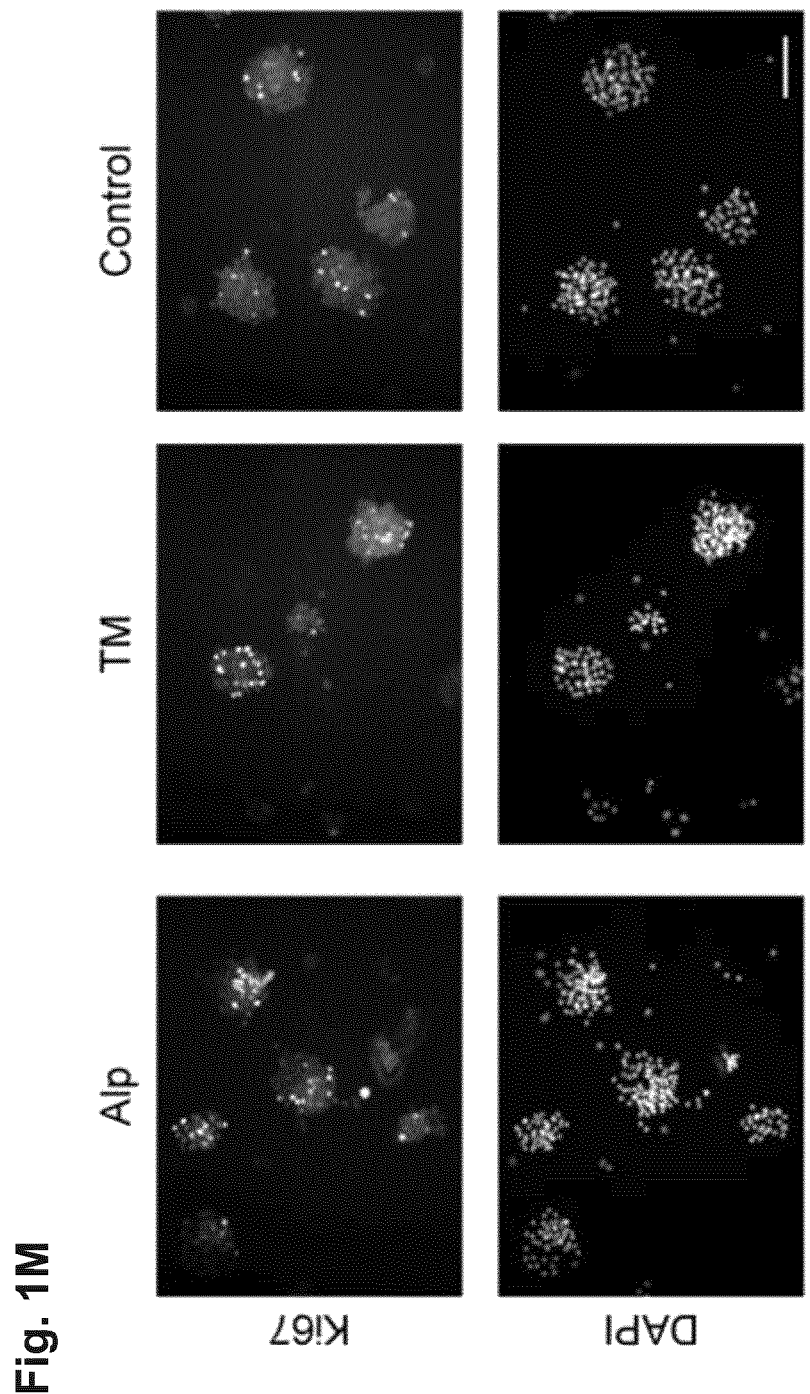

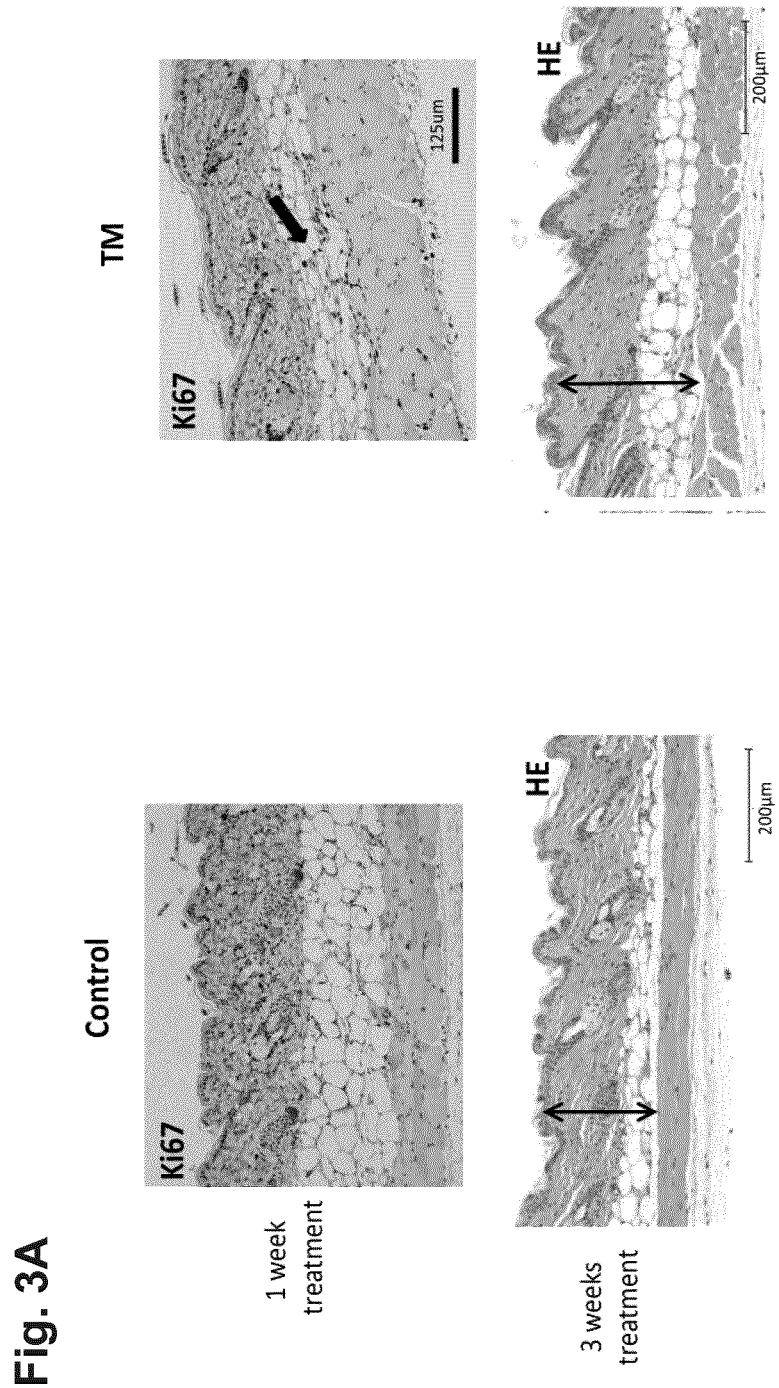

COMPOSITIONS AND METHODS FOR ENHANCING HAIR GROWTH, PROMOTING SKIN REGENERATION, AND WOUND HEALING

BACKGROUND

The non-limiting embodiments disclosed herein generally relate to compositions and methods useful for enhancing hair growth, promoting skin regeneration, and wound healing. The non-limiting embodiments disclosed herein also generally related to methods of screening for a compound capable of increasing cell proliferation.

There are inadequate methods for regenerating skin or inducing hair growth in a subject (e.g., for treatment of a disease or condition where regenerating skin or inducing hair growth is beneficial). In addition, impaired wound healing represents a significant cause of morbidity and mortality. The wound-healing process is a complex biological process where both differentiated and stem cells as well as cytokines/chemokines, growth factors, and skin matrix components are essential for effective wound healing. Expensive growth factors are often required for cell proliferation, and even then, expansion is often not optimal. Thus, molecules which replace or enhance the actions of growth factors and allow increased expansion of cells in culture, particularly stem cells such as skin-derived precursors (SKPs) are desirable.

Thus, there is a need for molecules that promote the proliferation and self-renewal of cells, such as SKPs. These molecules may be highly advantageous for cosmetic and medical purposes (e.g., hair growth, skin regeneration, and wound healing).

SUMMARY

In a first aspect described herein, there is provided a method of promoting skin repair or wound healing, the method including administering to a subject in need thereof a composition including an effective amount of trimebutine or a pharmaceutically acceptable salt or active metabolite thereof.

In certain non-limiting embodiments, the subject has a burn or an ulcer, has or previously had an infection resulting in skin loss, has undergone a surgical procedure requiring skin repair, or has an injury resulting in skin loss. In particular embodiments, the composition is administered until the wound substantially heals.

In a second aspect described herein, there is provided a method of promoting hair growth or treating a condition associated with hair loss, the method including administering to a subject in need thereof a composition including an effective amount of trimebutine or a pharmaceutically acceptable salt or active metabolite thereof.

In particular non-limiting embodiments, the condition associated with hair loss is selected from the group consisting of: androgenic alopecia, alopecia areata, anagen effluvium, self-induced hair loss, telogen effluvium, scarring alopecia, hair loss as a result of chemotherapy or radiation treatment, supplementing hair transplant, priming skull, administration after hair transplant, and hair loss as a result of exposure to toxic chemicals. In certain non-limiting embodiments, the compositions is administered until a symptom of hair loss improves, wherein the symptom of hair loss is selected from the group consisting of: gradual thinning on the top of the head, circular or patchy bald spots, sudden loosening of hair, full body hair loss, and excessive shedding of hair.

In another non-limiting embodiment, described herein the above method further includes monitoring whether the subject experiences an improvement in hair growth, wherein the improvement in hair growth is selected from the group consisting of: increase in hair density, increase in terminal hair density, vellus hair density or cumulative hair thickness, increase in anagen hair count, decrease in telogen hair count, increase in total hair count, and increase in linear hair growth rate.

In yet other non-limiting embodiments of the above method, the composition is administered with a second agent, wherein the second agent is selected from the group consisting of: alprostadil, finasteride, a type 2 5-alpha-reductase inhibitor, dutasteride, a type 1 and 2 5-alpha-reductase inhibitor, flutamide, bicalutamide, a pregnane derivative, a progesterone derivative, a diuretic, and a potassium channel opener.

In all non-limiting embodiments, the trimebutine can be trimebutine maleate or N-desmethyl trimebutine. In particular non-limiting embodiments, the subject is a human. In some non-limiting embodiments, the composition is formulated as a gel, cream, lotion, ointment, foam, powder, solution, spray, emulsion, or suspension for topical administration. In other non-limiting embodiments, the composition is formulated as a gel for topical administration. In other non-limiting embodiments, the composition includes from about 2% (v/v) to about 50% (v/v) (e.g., from about 2% (v/v) to about 5% (v/v), from about 2% (v/v) to about 10% (v/v), from about 2% (v/v) to about 20% (v/v), from about 5% (v/v) to about 10% (v/v), from about 10% (v/v) to about 15% (v/v), from about 10% (v/v) to about 20% (v/v), from about 15% (v/v) to about 20% (v/v), from about 20% (v/v) to about 30% (v/v), from about 25% (v/v) to about 30% (v/v), from about 30% (v/v) to about 35% (v/v), from about 35% (v/v) to about 40% (v/v), from about 40% (v/v) to about 45% (v/v), from about 45% (v/v) to about 50% (v/v)) of trimebutine maleate. In yet other non-limiting embodiments, the composition is formulated for oral administration, wherein the composition includes from about 5 mg to about 800 mg (e.g., from about 5 mg to about 10 mg, from about 5 mg to about 15 mg, from about 10 mg to about 15 mg, from about 10 mg to about 20 mg, from about 15 mg to about 20 mg, from about 20 mg to about 25 mg, from about 20 mg to about 30 mg, from about 25 mg to about 30 mg, from about 30 mg to about 35 mg, from about 30 mg to about 40 mg, from about 50 mg to about 100 mg, from about 100 mg to about 200 mg, from about 200 mg to about 300 mg, from about 300 mg to about 400 mg, from about 400 mg to about 600 mg, from about 600 mg to about 800 mg) of trimebutine maleate.

In any non-limiting embodiments, the composition can be administered one or more times a day. In some non-limiting embodiments, the composition is administered for at least two to twenty days. In other non-limiting embodiments, the composition is administered for more than twenty days. In any non-limiting embodiments, the composition can increase SKPs proliferation or SKPs activity.

In a third aspect described herein, there is provided a method of screening for a compound capable of increasing cellular proliferation, the method including contacting SKPs with (a) a first agent selected from trimebutine or an analog thereof, alprostadil, finasteride, a type 2 5-alpha-reductase inhibitor, dutasteride, a type 1 and 2 5-alpha-reductase inhibitor, flutamide, bicalutamide, a pregnane derivative, a progesterone derivative, a diuretic, and a potassium channel opener, and (b) a candidate compound; and determining the proliferation rate of the SKP, in which an increase in the proliferation rate of the SKPs in the presence of the candidate compound relative to the first agent alone indicates that the candidate compound increases cellular proliferation.

In all non-limiting embodiments, the trimebutine can be trimebutine maleate or N-desmethyl trimebutine.

These and other aspects and features will now become apparent to those skilled in the art upon review of the following description of specific non-limiting embodiments in conjunction with the accompanying drawings.

Definitions

As used herein, the term "administration" or "administering" refers to a method of giving a dosage of a composition to a subject. The method of administration may depend on a variety of factors, e.g., the components of the composition and the nature and severity of the disease, disorder, or condition. The phrase "administered together" means that two or more active agents (e.g., any of the compounds described herein) are formulated together in a single composition or two or more active agents (e.g., any of the compounds described herein) are administered in combination to the subject.

By "subject" is meant a human or non-human animal (e.g., a mammal).

By "topical application" is meant directly laying on or spreading on outer skin using, e.g., by use of the hands or an applicator such as a wipe, puff, roller, or spray.

By "cosmetically-acceptable" is meant product(s) or compound(s) suitable for use in contact with tissues (e.g., the skin) without undue toxicity, incompatibility, instability, irritation, and/or allergic response. The term is not intended to limit the ingredient/product to use solely as a cosmetic (e.g., the ingredient/product may be used a pharmaceutical).

By "topical carrier" or "dermalogically-acceptable carrier" is meant that the carrier is suitable for use in contact with dermal tissue without undue toxicity, incompatibility, instability, allergic response, and the like. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, maltose, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, polypropylene glycol, polyethylene glycol, propylene glycol, polyacrylic acid (carbomer), stearyl alcohol, isopropyl alcohol, cetyl alcohol, coconut oil, tea tree oil, aloe, wheat germ oil, ceteareth-15, and xylitol.

By "prevention" is meant that a prophylactic treatment is given to a subject who has or will have a disease, a disorder, a condition, or one or more symptoms associated with a disease, a disorder, or a condition.

By "reduction or reducing" of a disease, a disorder, or a condition is meant that the extent and/or undesirable clinical manifestations of the disease, disorder, or condition are lessened and/or the time course of the progression is slowed or lengthened, as compared to the extent or time course in the absence of treatment.

As used herein "hair" means scalp, head, facial, and/or body hair, including but not limited to the scalp, eye lashes, brows, mustache, beard, ear, nasal, chest, pubic, auxiliary, and the like.

By "effective amount" is meant an amount of a physiologically active compound or composition sufficient to induce a positive modification in the condition to be regulated or treated, (e.g., hair growth or wound healing) but low enough to avoid serious side effects. A safe and effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

By "trimebutine" is meant the free base of trimebutine, salts of trimebutine, or active metabolites of trimebutine. Salts and active metabolites of trimebutine described herein include but are not limited to trimebutine maleate (TM) or N-desmethyl trimebutine.

By "inducing or promoting hair growth" is meant the earlier induction of growth of a new hair cycle, and/or prolonging the active growth phase (anagen) of the hair cycle, and/or increasing the growth rate of the hair, and/or increasing the width of the hair shaft, including, but not limited to, the induction of the growth of hair and making it more visible to the eye. As used herein "improving hair quality" means increasing the diameter of the hair shaft and/or enhancing the visual attributes of the hair like hair volume, hair shine, and hair thickness, and/or affecting the characteristics of the hair shaft, and/or hair cuticles, including, but not limited to, creating a smoother look or feel, and/or increase in shine.

By "treatment" is meant an approach for obtaining beneficial or desired results, such as clinical results. Beneficial or desired results can include, but are not limited to, alleviation, amelioration, or prevention of a disease, a disorder, a condition, or one or more symptoms associated with a disease, a disorder, or a condition; diminishment of extent of disease, disorder, or condition; stabilization (i.e., not worsening) of a disease, disorder, or condition; delay or slowing the progress of a disease, disorder, or condition; and amelioration or palliation of a disease, disorder, or condition. "Treatment" can also mean prolonging survival as compared to expected survival if not receiving treatment.

By "small molecule" is meant a molecule having a molecular weight of less than about 1000 Da (e.g., less than 900, 800, 700, 600, 500, or 400 Da).

Compounds described herein include those described herein in any of their pharmaceutically acceptable forms, including isomers such as diastereomers and enantiomers, salts, esters, amides, thioesters, solvates, and polymorphs thereof, as well as racemic mixtures and pure isomers of the compounds described herein. As an example, by "trimebutine maleate" is meant the free base as well as any pharmaceutically acceptable salt thereof.

The term "pharmaceutically acceptable salt" represents those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared in situ during the final isolation and purification of the compounds described herein, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, isethionate, lactobionate, lactate, laurate, lauryl sulfate, malate, maleate, malonate, mesylate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In the generic descriptions of compounds described herein, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-12}$ heteroalkyl, for example, includes from 1 to 12 carbon atoms in addition to one or more heteroatoms. Other numbers of atoms and other types of atoms may be indicated in a similar manner.

The recitation herein of numerical ranges by endpoints is intended to include all numbers subsumed within that range (e.g. a recitation of 1 to 5 includes 1, 1.5, 2, 2.75, 3, 3.80, 4, and 5).

As used herein, "a" or "an" means "at least one" or "one or more" unless otherwise indicated. In addition, the singular forms "a", "an", and "the" include plural referents unless the context clearly dictates otherwise.

BRIEF DESCRIPTION OF THE FIGURES

FIGS. 1A-1O show the identification of drugs (e.g., trimebutine maleate (TM) and alprostadil (Alp)) that increase SKPs activity in a high-throughput drug screen. FIGS. 1A-1E are graphs showing the dose-response effect of Alp, TM, kaempferol (Kae), MG624, and pramoxine (Pram), respectively, on sphere number in human SKPs cultures. FIGS. 1J and 1K are graphs showing the effects of ALP, TM, or ALP and TM combined on SKP sphere number and sphere size, respectively. FIG. 1L is a graph showing the effects of ALP, TM, or latanoprost (Latan) on SKP sphere number. FIGS. 1M and 1N are an image and a graph showing an increase in Ki67+ cells in the wound bed of mice treated with Alp or TM. FIG. 1O is a graph showing that Ki67-positive NIH-3T3 cells were unaffected by Alp or TM treatment.

FIGS. 2A and 2B are plots showing the percentage wound closure in mice treated with TM or Alp compared to control at day 7 or day 9 post-wounding, respectively. FIG. 2C is images showing the morphometric analysis of wound gap and width in mice treated with Alp or TM 9 days post-wounding. NE indicates the new epithelium, RD indicates the regenerating dermis, and OW indicates the borders of the original punch wound. FIGS. 2D-2F are graphs showing the effects of Alp or TM on wound width, epithelial gap, and new dermal tissue at day 9 post-wounding. FIGS. 2G and 2H are images and a graph showing an increase in Ki67+ cells in the wound bed of mice treated with Alp or TM. FIGS. 2I and 2J are an image and a graph showing an increase in CD-31+ blood vessels in the wound bed of mice treated with Alp or TM. LE indicates the leading edge of the new epidermis, and RD the regenerating dermis.

FIGS. 3A-3C show the effects of topical application of TM or Alp on dermal maintenance in mice by increasing dermal proliferation and thickness. FIG. 3A is an image showing an increase in Ki67+ cells in the dermis in a 1 week treatment with TM and an image showing the dermal thickness as measured after a 3 week treatment with TM. FIG. 3B is a plot showing the number of dermal Ki67+ cells after 1 week topical application of Alp or TM. FIG. 3C is a plot showing the dermal thickness after 3 weeks topical application of Alp or TM.

FIG. 7A is an image of a gene expression heatmap and hierarchical clustering of SKP populations showing the transcriptional similarity in Alp-treated and TM-treated wounded and not wounded skin compared to control skin. FIG. 7B is a diagram showing overlap in the number of differentially expressed genes in wounded SKPs treated with Alp and TM for 7 days compared to control skin. FIGS. 7C and 7D is a diagram and an image of a gene expression heatmap showing the differential gene expression in wounded SKPs treated with Alp and TM for 24 hours compared to control skin. FIG. 7E is a diagram showing overlap in the top 50 differentially expressed genes in wounded SKPs treated with Alp and TM for 24 hours compared to control skin.

FIGS. 8A and 8B are an image of a western blot and a graph of scanning densitometry showing that SKPs exhibited an increase in ERK1/2 phosphorylation after treatment with Alp or TM. FIG. 8C is an image of a western blot showing that neither Alp nor TM increased phosphorylated, activated STAT3, GSK3beta, Akt1, or CREB compared to control. FIG. 8D is an image of a western blot showing that trametinib (MEKi) inhibited ERK1/2 phosphorylation in cultured SKPs. FIGS. 8E and 8F are graphs showing that MEKi decreased both the number and size of SKP clonal spheres. FIGS. 8G and 8H are an image and a graph showing that MEK inhibition decreased SKPs proliferation by immunostaining with Ki67. FIG. 8I is an image of a western blot showing that ERK1/2 phosphorylation in the presence of Alp and TM was suppressed by MEKi incubation. FIG. 8J is a graph showing that incubation with MEKi decreased sphere number, and neither Alp nor TM compensated for MEK inhibition. FIG. 8K is an image of a gene expression heatmap showing that MEKi resulted in an overall decrease in downstream gene expression in SKPS cultured in TM for 24 hours (heat map).

DETAILED DESCRIPTION

Figure 1G:
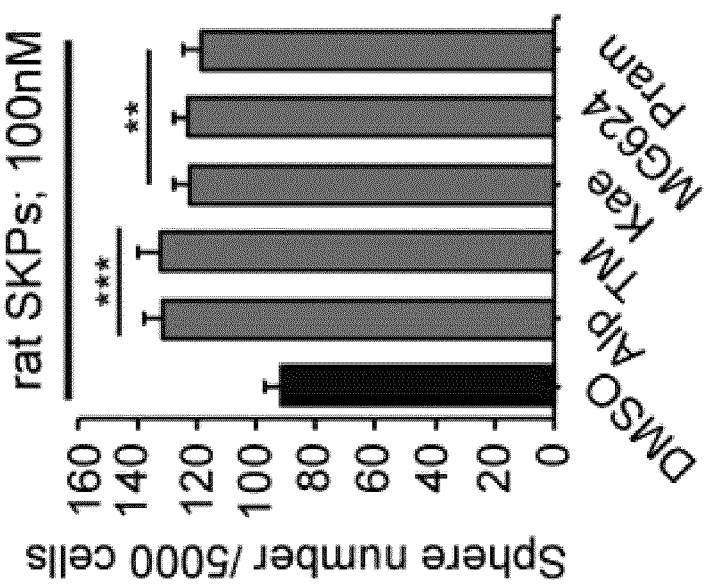
FIG. 1G is a graph showing the increase in rat SKPs sphere number after treatment with 100 nM of Alp, TM, Kae, MG624, or Pram.

We have discovered pharmacological agents from a high throughput drug screen that can increase skin-derived precursor cell (SKP) activity. SKPs are a population of skin-derived precursor cells which are found in adult mammalian tissues that play a crucial role in tissue maintenance and repair. In adult mammals, these tissue precursor cells become depleted over time or during pathological conditions and their depletion affect the ability of these cells to repair and maintain a specific tissue. SKPs are located in the dermis, particularly in the dermal papilla and dermal sheath and are able to differentiate in a variety of cell types. We previously have shown that SKPs when transplanted in the dermis can induce formation of new hair follicles and induce hair to grow. In addition, we have also shown that SKPs can generate new cells to replenish and maintain the dermis and participate in skin wound healing (Biernaskie et al., Cell Stem Cell. 5:610-623, 2009). It was also shown that genetic depletion of SKPs causes premature hair and skin aging (Su et al., Cell Stem Cell. 5:64-75, 2009). In light of these previous discoveries, the goal of the non-limiting embodiment described herein is to recruit endogenous SKPs by using pharmacological agents (e.g., small molecule compounds) that increase SKPs activity to be able to enhance tissue repair and regeneration. Accordingly, the non-limiting embodiments described herein feature compositions including trimebutine maleate, other trimebutine salts, and active metabolites thereof that are useful in promoting hair growth, treating conditions associated with hair loss, and promoting wound healing and skin regeneration.

Trimebutine Salts and Derivatives Thereof

In a non-limiting embodiment described herein features compositions comprising trimebutine (also referred to as 3,4,5-trimethyoxy benzoic dimethyl amido-2-phenyl butylester; 3,4,5-trimethyoxybenzoic acid 2-(dimethylamino)-2-phenylbutyl ester; or 2-(Dimethylamino)-2-phenylbutyl 3,4,5-trimethoxybenzoate), the free base, salts thereof, or active metabolites thereof. Active metabolites of trimebutine include N-desmethyl trimebutine (also referred to as nor-trimebutine) and their corresponding stereoisomers, (R)—N-desmethyl trimebutine and (S)—N-desmethyl trimebutine. Salts of trimebutine include trimebutine maleate (TM) and any of the compounds disclosed in U.S. Pat. No. 7,666,907, which is herein incorporated by reference.

Cells

The compounds identified herein may be used to increase proliferation of stem cells, such as SKPs. SKPs are described in U.S. Patent Application Publication Nos. 2004/0033597 and 2007/0248574. SKPs can express at least one, two, three, or more of the following molecular markers: nestin, WNT-1, vimentin, versican, fibronectin, S100β, slug, snail, twist, Pax3, Sox9, Dermo-1, and Sox2. SKPs may also express increased levels of slug, snail, twist, and Pax3 relative to central nervous system neural stem cells. Desirably, the multipotent stem cells described herein do not express measurable levels of at least one, two, three, or more of the following molecular markers: tyrosinase, c-kit, tryp-1, and DCT, which are markers of melanoblasts and melanocytes. The multipotent stem cells also may not express of one or more of the following markers of Schwann cells: MBP, P0, p75NTR, and Sox10.

SKPs are capable of differentiating into various non-neural cells (e.g., hair follicle cell, bone cell, smooth muscle cell, or adipocyte) and neural cells (e.g., a neuron, astrocyte, Schwann cell, or oligodendrocyte).

SKPs can be isolated as described in the art. In one example, dorsal or facial skin from mouse embryos (E15-19), mouse or rat neonates (P2-P6), or adults (3 weeks and older) was dissected from the animal and cut into 2-3 mm² pieces. Tissue was digested with 0.1% trypsin for 10-45 min at 37° C., mechanically dissociated and filtered through a 40 μm cell strainer (Falcon).

Cell Culture

The cells (e.g., SKPs) may be cultured under standard cell culture conditions, such as those described herein or known in the art. In one example, SKPs are cultured as described in Toma et al. (Nat. Cell Biol. 3:778-784, 2001). Dissociated cells (e.g., as described above) were pelleted and plated in DMEM-F12, 3:1 (Invitrogen), containing 20 ng/ml EGF and 40 ng/ml FGF2 (both from Collaborative Research), hereafter referred to as proliferation medium. Cells were cultured in 25 cm² tissue culture flasks (Falcon) in a 37° C., 5% $CO_2$ tissue culture incubator. SKPs were passaged by mechanically dissociating spheres and splitting 1:3 with 75% new medium and 25% conditioned medium from the initial flask. For neuronal differentiation, SKP spheres or primary dissociated skin cells were mechanically dissociated and plated on chamber slides (Nunc) coated with poly-D-lysine/laminin in DMEM-F12 3:1 supplemented with 40 ng/ml FGF2 and 10% FBS (BioWhittaker) for 5-7 days. Cells were then cultured an additional 5-7 days in the same medium without FGF2 but with the addition of 10 ng/ml NGF (Cedar Lane), 10 ng/ml BDNF (Peprotech), and 10 ng/ml NT3 (Peprotech). For Schwann cell differentiation, dissociated spheres were cultured in DMEM-F12 3:1 supplemented with 10% FBS for 7 days, then switched to the same medium supplemented with 4 μM forskolin (Sigma).

Treatment of Subjects

Hair Growth and Conditions Associated with Hair Loss

The compounds and compositions described herein are useful for inducing hair growth and for the treatment of various types of alopecia and other conditions associated with hair loss. Alopecia is the most common hair growth disorder in humans. Hair loss most commonly occurs from the scalp. However, any hair-bearing area can be affected, including eyebrows, eyelashes, beard, and body areas. Alopecia can be divided into disorders in which the hair follicle is normal but the cycling of hair growth is abnormal, and disorders in which the hair follicle is damaged. Six major types of alopecia are known: androgenic alopecia, alopecia areata, anagen effluvium, self-induced hair loss, telogen effluvium, and scarring alopecia.

Androgenetic alopecia includes male pattern baldness and female pattern baldness. Androgenetic alopecia accounts for 95% of all hair loss. This genetically determined disorder is progressive through the gradual conversion of large, thick, pigmented, terminal hairs into thinner, shorter, indeterminate hairs and finally to short, wispy, non-pigmented, vellus hairs. Patients have a reduction in the terminal-to-vellus hair ratio, normally at least 2:1. Following miniaturization of the follicles, fibrous tracts remain. Patients with this disorder usually have a typical distribution of hair loss.

Male pattern alopecia begins with the recession of the hairline and results in complete hair loss, while female pattern alopecia causes diffuse thinning of the hair at and behind the hairline and there is no recession of the hairline. Male pattern alopecia begins in the late teens and early 20's when the testosterone levels are high, while female pattern alopecia begins in the late 30's and reaches its peak after 50 when testosterone levels are falling. Male pattern alopecia affects up to 70% of all males, whereas female pattern alopecia affects up to 30% of women. Females with predisposition for male pattern alopecia rapidly develop typical male pattern baldness if given high doses of testosterone.

Alopecia areata is thought to be an autoimmune disease in which T-lymphocytes attack the hair follicles, causing the hair to stop growing and enter into the telogen phase. At the end of the telogen phase, the hair falls out. Alopecia areata affects both men and women equally and is often experienced first in childhood. There are three subtypes of alopecia areata which are named according to their severity: (i) Alopecia areata, which involves mild patchy hair loss on the scalp; (ii) Alopecia totalis which involves loss of all scalp hair; and (iii) Alopecia universalis which involves loss of scalp and all body hair.

Anagen effluvium is the sudden hair loss, which occurs as a result of exposure to chemicals or radiation, such as the hair loss that results during certain types of chemotherapy or radiation treatment, or as a result of exposure to toxic chemicals such as thallium and arsenic. In anagen effluvium the hair does not enter a resting stage. The hair loss is usually sudden occurring 1 to 3 weeks after expose to the chemicals or radiation has occurred. In most cases hair growth will return to normal once treatment is finished. The drugs which are most likely to cause hair loss include amsacrine; cis-platinum; cytosine arabinoside; cyclophosphamide; doxorubicin; epirubicin; etoposide ifosfamide; and vincristine. It has been found that agents which protect against alopecia induced by a particular drug may be ineffective in protecting against a different drug. For example, a composition obtained from the bacteria *Serratia marcescens* has been used to protect against the alopecia which is associated with the use of cytosine araginoside and doxorubicin. This composition had no effect on alopecia which was induced by cyclophosphamide.

Self-induced hair loss may be inflicted consciously or unconsciously. The two main types of self-induced hair loss are trichotillomania and traction alopecia. Trichotillomania is self-induced hair loss which results from the continuous pulling or plucking of the hair. It occurs most commonly among young children, adolescents and women and affects twice as many females as males. The hair is often pulled out in distinct patches on the scalp. Some individuals also pull out eyebrows and eyelashes. The treatment for trichotillomania often involves counseling or psychiatric help, whereby in some cases an antidepressant is prescribed. Traction alopecia is usually caused by continuous and excessive pulling on the hair due to various types of hairstyling, which gradually results in hair loss that may become permanent. Generally, a change in hairstyle that reduces the traction on the hair and hair follicle is sufficient to reverse the hair loss in this case.

Telogen effluvium is sudden or severe stress related hair loss, which appears as thinning throughout the whole scalp. A sudden or stressful event can cause the hair follicles to prematurely stop growing and enter into a resting phase. The hair will then stay in the resting phase for about 3 months after which time a large amount of hair will be shed. In most cases the hair loss is temporary and the hair soon recovers. In some cases, the hair loss continues until the underlying cause is removed. Events which may lead to telogen effluvium include childbirth; termination of pregnancy; starting or stopping birth control pills; use of various medications; and severe emotional stress. Increased levels of hormones estrogen and progesterone during pregnancy cause more hairs than normal to remain in the growth phase. Following childbirth or termination of pregnancy, many of the hair follicles that had delayed entering the resting phase suddenly enter the resting phase due to the rapid drop in hormone levels. Drugs which may cause hair loss as a side effect include anti-gout agents such as alloppurinol; blood thinners such as heparin and coumarin; and cholesterol lowering drugs such as clofibrate and gemfibrozil. Telogen effluvium may also occur after a traumatic event such as the death of a loved one, an accident, abuse or any other severely traumatic event. These events may trigger the hair follicles to enter the resting phase prematurely in which case an increase in the amount of hair shed will be noticed about 3 months after the event. Other causes of telogen effluvium include thyroid gland malfunction (hypothyroidism or hyperthyroidism, which occurs when the thyroid gland produces too little or too much, respectively, of the thyroid hormone, thyroxin); diabetes; anemia; and the autoimmune disease, systemic lupus erythematosis.

Scarring alopecia occurs as a result of inflammation of the hair follicles due to infection. Scarring alopecia may be caused by discoid lupus erythematosus, a diffuse connective tissue disease; lichenplanus, which is an inflammatory disease that strikes primarily the skin and mucous membranes; Pseudopelade of Brocq, a rare scarring alopecia which has no potential for regrowth; aplasia cutis congenita, a rare disorder that often results as a small blistered atrophied area usually in the midline of the scalp and present from birth; or congenital ctrichia. Other types of hair loss include syphilitic alopecia, a secondary manifestation of syphilis; scleroderma; and tinea capitis (ringworm).

The compositions described herein are also useful in supplementing hair transplant, priming skull and can be administered after hair transplant.

Wound Healing and Skin Repair

The compounds and compositions described herein are also useful in promoting wound healing and skin repair. Depending on the healing time of a wound, it can be classified as acute or chronic. Those classified as acute wounds heal uneventfully (with no complications) in the predicted amount of time. Those classified as chronic wounds take a longer time to heal and might have some complications. Wounds can be open or closed. Open wounds are wounds with exposed underlying tissue and/or organs that are open to the outside environment (like penetrating wounds). Closed wounds have damage that occurs without exposing the underlying tissue and organs (non-penetrating wounds). Another way to classify wounds is to determine if the wound is clean or contaminated. Clean wounds have no foreign materials or debris inside, whereas contaminated wounds or infected wounds might have dirt, fragments of the causative agent, bacteria or other foreign materials.

Wound origin can be either internal or external. Internal wounds result from impaired immune and nervous system functions and/or decreased supply of blood, oxygen or nutrients to that area; such as in cases of chronic medical illness (diabetes, atherosclerosis, deep vein thrombosis).

External wounds are usually caused by penetrating objects or non-penetrating trauma, and other miscellaneous causes as follows: non-penetrating wounds are usually the result of blunt trauma or friction with other surfaces, the wound does not break through the skin, and may include abrasions (scraping of the outer skin layer), lacerations (a tear-like wound), contusions (swollen bruises due to accumulation of blood and dead cells under skin), concussions (damage to the underlying organs and tissue on head with no significant external wound); penetrating wounds result from trauma that breaks through the full thickness of skin, reaching down to the underlying tissue and organs, and includes stab wounds (trauma from sharp objects, such as knives), skin cuts, surgical wounds (intentional cuts in the skin to perform surgical procedures), gunshot wounds (wounds resulting from firearms); miscellaneous wounds may include thermal wounds from extreme temperatures, either hot or cold, can result in thermal injuries (like burns, sunburns and frostbite), chemical wounds result from contact with or inhalation of chemical materials that cause skin or lung damage, bites and stings from humans, dogs, bats, rodents, snakes, scorpions, spiders and ticks, and electrical wounds are usually present with superficial burn-like or sting-like wounds secondary to the passage of high-voltage electrical currents through the body, and may include more severe internal damage.

Monitoring of Subjects

The methods described herein can also include monitoring of hair loss, hair growth, and response to treatment with the compounds or compositions described herein. Quantitative methods for the analysis of human hair growth and hair loss are necessary to determine the efficacy of hair promoting drugs. The physician may evaluate the body and scalp hair distribution by different grading systems, hair pull test, dermatoscopy, and computer assisted phototrichogram. In some cases, trichogram and biopsies are also helpful tools. For research purposes, optical coherent tomography, electron microscopy, biochemical methods, atomic force microscopy, and confocal laser scanning microscopy can be used as methods for analyzing the structure of the hair. For clinical studies, global photographs, hair weighing, phototrichogramm, and different clinical scoring systems can also be used to monitor hair growth and response to treatment.

In any of the above mentioned methods for monitoring hair loss, hair growth, and response to treatment, an improvement in hair growth or a positive response to treatment is determined as increase in hair density, increase in terminal hair density, vellus hair density or cumulative hair thickness, increase in anagen hair count, decrease in telogen hair count, increase in total hair count, and increase in linear hair growth rate.

Assessment of wound healing can additionally be performed on the subjects prior to, during, and subsequent to administration of the compounds and compositions described herein. Wound healing can be monitored using the instruments and tools described below.

The pressure ulcer scale for healing (PUSH) is a tool designed to track pressure ulcer healing by monitoring wound parameters of length times width, exudates amount, and tissue type. The PSST is designed to describe wound healing in pressure ulcers, consisting of 15 scored and two non-scored items. The scored items assessed variables of wound size and depth, tissue characteristics and wound exudates, and the non-scored items examined wound location and shape. The sessing scale (SS) is a seven-stage scale designed to measure progress in wound healing over time, with each stage describing wound tissue attributes throughout the wound healing process. The Sussman Wound Healing Tool (SWHT) is based on an acute model of wound healing, which describes tissue status and size throughout the wound healing process. The tool itself consists of 21 items, gathering data on wound attributes, location, healing phase, and extent of tissue damage. The wound healing scale (WHS) is an alternative tool to the reverse staging of pressure ulcers. The scale is based upon the existing NPUAP staging system, with eight alphabetic modifiers that reflect the physiological changes that occur with healing. The Barber Measuring Tool (BMT) track changes in wound volume over time, with wound progression presented as percentage healed over time.

For an assessment of wound healing, the time it takes for a wound to heal can also be a measure of the efficacy of the treatment with the compositions described herein. Wound healing can be measured by the amount of days it takes to go through the stages of healing (e.g., hemostasis, inflammation phase, proliferation phase, and remodeling or maturation phase) or can be a qualitative observation of the amount of days it takes for the symptoms of a wound to diminish and the damaged area to visually heal (e.g., no swelling, no redness, no bleeding, no pain or tenderness). Treatment with the compositions described herein can decrease the days for a wound to heal by, for example, 2, 3, 4, 5, 6, 7, 8, 9, 10 days, as compared to the days for a wound to heal without treatment.

Combination Therapy

The compositions described herein may also be used in combination with compounds known to promote hair growth that are available as drugs, such as finasteride (Propecia), a type 2 5-alpha-reductase inhibitor, and dutasteride, a type 1- and 2-5-alpha-reductase inhibitor, as well as flutamide, bicalutamide, pregnane derivatives, progesterone derivatives, experimental agents, such as FCE 28260, and the like. Spironolactone and other diuretics may also be utilized as it is indicated for women in some cases (also known as Aldactone: an aldosterone receptor antagonist). Potassium channel openers, such as Minoxidil (Rogaine), which are known to promote hair growth are also believed to be especially promising combinations. Herbal remedies that may have 5-alpha reductase inhibitory action may include: Saw Palmetto and *Pygeum africanum*. Other agents that may have such activity are Beta-sisterol, Sepicontrol and Licorice, gamma-linolenic acid, zinc and zinc salts, green tea catechin(-)-epigallocatechin gallate (EGCG), and other unsaturated fatty acids (Tehming LIANG and Shut-sung LIAO) Biochem. J. (1992) 285, 557-562). Grape seed, apple seed, apple juice and barley extracts may also be potential agents that may induce hair growth.

Additional combinations may include other known stimulators of hair growth, such as zinc, calcineurin inhibitors, such as FK506 (Tacrolimus, Fujimycin), a macrolide antibiotic produced by *Streptomyces tsukubaensis*, and its derivatives, or Cyclosporin A, a cyclic endecapeptide, alprostadil, latanoprost, and a T cell-specific immunosuppressant, and the like.

Formulations of Pharmaceutical Compositions

The administration of any compound or composition described herein may be by any suitable means that results in a concentration of the compound that increases cellular proliferation, enhances skin repair or skin health, or promotes hair growth. The compound may be contained in any appropriate amount in any suitable carrier substance, and is generally present in an amount of 1-95% by weight of the total weight of the composition. The composition may be provided in a dosage form that is suitable for the oral, skin (e.g., topical or by patch), cutaneous, parenteral (e.g., intravenous or intramuscular), rectal, nasal, vaginal, inhalant, ocular, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Pharmaceutical compositions may be formulated to release the active compound immediately upon administration or at any predetermined time or time period after administration. The latter types of compositions are generally known as controlled release formulations, which include (i) formulations that create substantially constant concentrations of the agent(s) described herein within the body over an extended period of time; (ii) formulations that after a predetermined lag time create substantially constant concentrations of the agents described herein within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the compound to a particular target cell type. For compounds having a narrow absorption window in the gastro-intestinal tract or a relatively short biological half-life, administration of the compound can be in the form of a controlled release formulation.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, molecular complexes, microspheres, nanoparticles, patches, and liposomes.

Topical Formulations

Pharmaceutical compositions described herein can be formulated for topical administration. Subjects can be administered effective amounts of a compound described herein by means of topical application to the skin. The compositions described herein may be made into a wide variety of product types that include but are not limited to solid and liquid compositions such as lotions, creams, gels, sticks, sprays, ointments, cleansing liquid washes and solid bars, shampoos, pastes, powders, foams, mousses, and wipes. These product types may contain several types of cosmetically acceptable topical or dermalogically acceptable carriers including, but not limited to solutions, emulsions (e.g., microemulsions and nanoemulsions), gels, solids and liposomes. The following are non-limiting examples of such carriers. Other carriers can be formulated by those of ordinary skill in the art.

The topical compositions described herein can be formulated as solutions. Solutions can include an aqueous solvent (e.g., from about 50% to about 99.99% or from about 90% to about 99% of a cosmetically acceptable aqueous solvent). Such compositions can contain about 30% solvent, although this may vary dependent upon the formulation. Such solvents may include ethanol, propylene glycol, polyethylene glycol, mixtures thereof and the like which are good carriers for successful delivery to the hair follicles. Preferably, the compositions described herein are formulated with: from about 20% (v/v) to about 50% (v/v) propylene glycol (e.g., from about 20% (v/v) to about 30% (v/v), from about 25% (v/v) to about 30% (v/v), from about 30% (v/v) to about 35% (v/v) from about 35% (v/v) to about 40% (v/v), from about 40% (v/v) to about 45% (v/v), from about 45% (v/v) to about 50% (v/v)), from about 10% (v/v) to about 40% (v/v) ethanol (e.g., from about 10% (v/v) to about 15% (v/v), from about 15% (v/v) to about 20% (v/v), from about 20% (v/v) to about 25% (v/v), from about 25% (v/v) to about 30% (v/v) from about 30% (v/v) to about 35% (v/v), from about 35% (v/v) to about 40% (v/v)), and from about 10% to about 70% (v/v) water (e.g., from about 10% (v/v) to about 15% (v/v), from about 15% (v/v) to about 20% (v/v), from about 20% (v/v) to about 25% (v/v), from about 30% (v/v) to about 35% (v/v), from about 35% (v/v) to about 45% (v/v), from about 45% (v/v) to about 55% (v/v), from about 55% (v/v) to about 65% (v/v), from about 60% (v/v) to about 70% (v/v)).

Topical compositions may also be formulated as a solution containing an emollient. Such compositions can contain from about 2% to about 50% of an emollient(s). As used herein, "emollients" refer to materials used for the prevention or relief of dryness, as well as for the protection of the skin. A wide variety of suitable emollients are known and may be used herein. The International Cosmetic Ingredient Dictionary and Handbook, eds. Wenninger and McEwen, pp. 1656-61, 1626, and 1654-55 (The Cosmetic, Toiletry, and Fragrance Assoc, Washington, D. C, 7$^{th}$ Edition, 1997) contains numerous examples of suitable materials. A lotion may be made from a solution. Lotions typically contain from about 1% to about 20% (more preferably, from about 5% to about 10%) of an emollient(s) and from about 50% to about 90% (more preferably, from about 60% to about 80%) of water. The compositions described herein may be formulated as a cream. A cream typically comprises from about 5% to about 50% (more preferably, from about 10% to about 20%) of an emollient(s) and from about 45% to about 85% (more preferably, from about 50% to about 75%) of water. Yet another type of product that may be formulated from a solution is an ointment. An ointment may be constituted of a simple base of animal or vegetable oils or semi-solid hydrocarbons. An ointment may contain from about 2% to about 10% of an emollient(s), and from about 0.1% to about 2% of a thickening agent(s). The INCI Handbook, supra, contains a list of acceptable thickening agents or viscosity increasing agents useful in the compositions and methods described herein.

The topical compositions described herein may also be formulated as emulsions. If the carrier is an emulsion, from about 1% to about 10% (more preferably from about 2% to about 5%) of the carrier should be made up one or more emulsifiers. Emulsifiers may be nonionic, anionic or cationic. Suitable emulsifiers may be found in, e.g., the INCI Handbook, pp 0.1673-1686.

Lotions and creams may also be formulated as emulsions. Typically such lotions can contain from 0.5% to about 5% of an emulsifier(s). Such creams can typically comprise from about 1% to about 20% (more preferably from about 5% to about 0%) of an emollient(s); from about 20% to about 80% (preferably, from 30% to about 70%) of water; and from about 1% to about 10% (more preferably, from about 2% to about 5%) of an emulsifier(s). Single emulsion skin care preparations, such as lotions and creams, of the oil-in-water type and water-in-oil type are well-known in the cosmetic art. Multiphase emulsion compositions, such as the water-in-oil-in-water type are also useful. In general, such single or multiphase emulsions contain water, emollients, and emulsifiers as essential ingredients.

Compositions described herein may also be in the form of shampoo, hair conditioning products, leave-on hair masks, mousse, sprays, in combination with dyes and other hair care products for cleaning, treating, conditioning and coloring the hair simultaneous with topical application of the compositions described herein.

The topical compositions described herein may be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose, hydroxypropyl cellulose, polypropylene glycol, polyethylene glycol, (PEG), or propylene glycol (PG)). Suitable gelling agents for oils (such as mineral oil) include, but are not limited to, hydrogenated butylene/ethylene/styrene copolymer and hydrogenated ethylene/propylene/styrene copolymer. Such gels typically comprises between about 0.1% and 5%, by weight, of such gelling agents. Microgels may be used to enhance follicular delivery of the formulations.

The topical compositions described herein may also be formulated into a solid formulation (e.g., a wax-based stick, mascara, soap bar composition, powder, or a wipe containing powder. The topical compositions described herein may contain, in addition to the aforementioned components, a wide variety of additional oil-soluble, organic solvent-soluble, and/or water-soluble materials conventionally used in compositions for use on skin and hair, at their art-established levels. For example, a formulation of 70% ethanol and 30% propylene glycol or variable amounts of these two agents may be used for enhanced delivery of the actives.

The compositions described herein may contain one or more surfactants. In one non-limiting embodiment, the composition may contain a lathering surfactant. A lathering surfactant is a surfactant that generates lather when combined with water and mechanically agitated. In one non-limiting embodiment, the lathering surfactant has an initial foam height reading of at least 20 mm, such as at least 50 mm, in the Standard Test Method for Foaming Properties of Surface-Active Agents D1173-53 Set forth in the ASTM Annual Book of ASTM Standards 1001 Section 15 Volume 15.04 (using a concentration of 5 grams per liter, temperature of 49° C., and water hardness of 8 grains per gallon). Examples of lathering surfactants include, but are not limited to, anionic, nonionic, cationic, and amphoteric lathering surfactants. Nonlimiting examples of anionic lathering surfactants include those selected from the group consisting of sarcosinates, sulfates, isethionates, taurates, phosphates, lactylates, and glutamates. Specific examples include, but are not limited to, those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof. Nonlimiting examples of nonionic lathering surfactants include those selected from the group consisting of alkyl glucosides, alkyl polyglucosides, polyhydroxy fatty acid amides, alkoxylated fatty acid esters, lathering sucrose esters, amine oxides, and mixtures thereof. Specific examples include, but are not limited to nonionic surfactants selected from the group consisting of C8-C14 glucose amides, C8-C14 alkyl polyglucosides, sucrose cocoate, sucrose laurate, lauramine oxide, cocoamine oxide, and mixtures thereof. Nonlimiting examples of amphoteric lathering surfactants (which also includes zwitterionic lathering surfactants are those selected from the group consisting of betaines, sultaines, hydroxysultaines, alkyliminoacetates, iminodialkanoates, aminoalkanoates, and mixtures thereof. Nonlimiting examples of amphoteric surfactants include disodium lauroamphodiacetate, sodium lauroamphoacetate, cetyl dimethyl betaine, cocoamidopropyl betaine, cocoamidopropyl hydroxy sultaine, and mixtures thereof.

The compositions described herein may further contain one or more additional cosmetically active agent (s) as well as the above-mentioned components. A cosmetically active agent is a compound, which may be a synthetic compound or a compound isolated, purified or concentrated from a natural source, or a natural extract containing a mixture of compounds, that has a cosmetic or therapeutic effect on the tissue, including, but not limited to: anti-microbial agents such as anti-yeast agents, anti-fungal, and anti-bacterial agents, antiinflammatory agents, anti-aging agents, anti-parasite agents, external analgesics, sunscreens, photoprotectors, antioxidants, keratolytic agents, detergents/surfactants, moisturizers, nutrients, vitamins, minerals, energy enhancers, anti-perspiration agents, astringents, hair growth enhancing agents, hair coloring agents, pigments, firming agents, agents for skin conditioning, anti-dandruff agent, and odor-control agents such as odor masking or pH-changing agents. In one non-limiting embodiment, the cosmetically active agent may be selected from, but not limited to, the group consisting of hydroxy acids, benzoyl peroxide, D-panthenol, octyl methoxycinnimate, titanium dioxide, octyl salicylate, homosalate, avobenzone, carotenoids, free radical scavengers, spin traps, retinoids such as retinoic acid (tretinoin) and retinoid precursors such as retinol and retinyl palmitate, vitamins such as vitamin E (alpha, beta or delta tocopherols and/or their mixtures) ceramides, polyunsaturated fatty acids, essential fatty acids, enzymes, enzyme inhibitors, minerals, hormones such as progesterones, steroids such as hydrocortisone, 2-dimethylaminoethanol, metal (including but not limited to iron or zinc) salts such as copper chloride, peptides containing copper such as Cu:Gly-His-Lys, coenzyme Q10, amino acids, vitamins, acetyl-coenzyme A, niacin, riboflavin, thiamin, ribose, electron transporters such as NADH and FADH2, botanical extracts such as aloe vera, Feverfew, and Soy, and derivatives and mixtures thereof. The cosmetically active agent can be present in the composition described herein in an amount of from about 0.001% to about 20% by weight of the composition, from about 0.005% to about 10%, or from about 0.01% to about 5%. Also expected to be particularly effective in the composition and methods described herein are the presence of synthetic or natural 5-alpha reductase inhibitors, or other anti-sebum ingredients including, but not limited to, Sepicontrol (Capryloyl Glycine, Sarcosine and *Cinamomum Zeylanicum* Bark Extract), licorice powder or extract, and the like.

Solid Dosage Forms for Oral Use

Formulations for oral use include tablets containing the active ingredient(s) in a mixture with non-toxic pharmaceutically acceptable excipients, and such formulations are known to the skilled artisan (e.g., U.S. Pat. Nos.: 5,817,307, 5,824,300, 5,830,456, 5,846,526, 5,882,640, 5,910,304, 6,036,949, 6,036,949, 6,372,218, hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or may be coated by known techniques, optionally to delay disintegration and absorption in the gastrointestinal tract and thereby providing a sustained action over a longer period. The coating may be adapted to release the compound in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols, and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes, (e.g., chemical degradation prior to the release of the active substances). The coating may be applied on the solid dosage form in a similar manner as that described in Encyclopedia of Pharmaceutical Technology, supra.

The compositions described herein may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

Parenteral Compositions

A composition containing a compound described herein or identified using the methods described herein may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Dosages

The dosage of any compound described herein depends on several factors, including: the administration method, the amount of increase in cellular proliferation, skin repair, hair growth, or skin health enhancement desired, and the age, weight, and health of the subject to be treated.

With respect to the treatment methods described herein, it is not intended that the administration of a compound to a subject be limited to a particular mode of administration, dosage, or frequency of dosing. Treatment methods described herein contemplate all modes of administration, including oral, cutaneous, subcutaneous, intramuscular, intravenous, intraperitoneal, intravesicular, intraarticular, intralesional, or any other route sufficient to provide a dose adequate to increase cellular proliferation, enhance skin repair or skin health, or promote hair growth treat. The compound may be administered to the subject in a single dose or in multiple doses. For example, a compound described herein may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compound. For example, the dosage of a compound can be increased if the lower dose does not provide sufficient activity in promoting hair growth or wound healing. Conversely, the dosage of the compound can be decreased if there is improvement in hair growth or wound healing as assessed by the methods described herein.

The compositions described herein may be administered in unit dosage form and may be prepared by any of the methods well-known in the pharmaceutical art, for example, as described in "Remington: The Science and Practice of Pharmacy" (20th ed., ed. A. R. Gennaro, 2000, Lippincott Williams & Wilkins). The concentration of at least one active compound in the formulation will vary depending upon a number of factors, including the dosage of the drug to be administered, and the route of administration.

The compounds described herein may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

The composition can be prepared in any useful method. For example, at least one therapeutic agent is dissolved in ethanol and added to a mixture of propylene glycol (PG) or polyethylene glycols (PEGs). In another example, the composition further includes a skin penetrating enhancer of a dimethyl alanine amide of medium chain fatty acids with carbon units varying between C-12 and C-16. More specifically, active compounds alone or combinations thereof may be prepared in an ointment form or a cream form. In these forms, the unit dosage of the therapeutic agent and vehicle can be in the range of 0.1 mg to 1000 mg and more preferred between 50 mg and 600 mg. For example, the dosages can contain from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient, from about 50 mg to about 300 mg, from about 50 mg to about 250 mg, from about 100 mg to about 300 mg, or from about 100 mg to about 250 mg, from about 100 mg to about 500 mg, from about 500 mg to about 1000 mg of the active ingredient.

The active compounds in the composition by weight can be in the range of 0.5% to 30% (v/v). A more preferred range would be between 5% and 20% (v/v). In another non-limiting embodiment, the composition comprises between 0.5%-2%, 1%-2%, 2.5%-5%, 8%-12%, 10%-20%, or 20-30% (v/v) of at least one compound (i.e., trimebutine maleate (TM)). In one implementation, the active compound is present in the composition in an amount of at least 0.5%, at least 1%, at least 2%, at least 2.5%, at least 3%, at least 5%, at least 10%, at least 15%, at least 20%, or at least 25% (v/v), and may be, for example, trimebutine maleate (TM) or N-desmethyl trimebutine.

Optimization of the appropriate dosages can readily be made by the skilled practitioner in light of the pharmacokinetics of the active compound or combination of active compounds used in the composition. Factors to be considered in setting dosages include the therapeutic agent's specific activity; the severity of the condition or symptoms of the subject; the age, condition, body weight, sex, and diet of the subject; the use (or not) of concomitant therapies; and other clinical factors.

Administration may be one or multiple times daily, weekly (or at some other multiple day interval) or on an intermittent schedule, with that cycle repeated a given number of times (e.g., 2-10 cycles) or indefinitely. The compositions can be administered for at least two days (e.g., 2 days, 3, days, 4 days, 5 days, one week, or two weeks). The compositions can be administered once daily or up to four times daily (e.g., once daily, twice daily, three times daily, or 4 times daily). The compositions may be administered as symptoms occur or until the symptoms subside. The compositions can also be administered chronically (e.g., more than twenty days, e.g., 21 days, 30 days, 60 days, 3 months, 6 months, 9 months, one year, two years, or three years). In one non-limiting embodiment, the composition comprises between 2% to 10% (v/v) of at least one active compound described herein (e.g., trimebutine maleate (TM) or N desmethyl trimebutine). In another embodiment, the total daily dose of the composition (e.g., trimebutine maleate (TM) or N-desmethyl trimebutine) described herein is from about 50 mg/daily to about 200 mg/daily (e.g., 50 mg/daily, 55 mg/daily, 60 mg/daily, 65 mg/daily, 70 mg/daily, 75 mg/daily, 80 mg/daily, 85 mg/daily, 90 mg/daily, 95 mg/daily, 100 mg//daily, 150 mg/daily, 160 mg/daily, 180 mg/daily, or 200 mg/daily).

EXAMPLES

Example 1

Screen for Compounds that Enhance Cellular Proliferation of SKPs

Given the potential clinical use of SKPs to enhance hair growth and skin morphogenesis, a high throughput drug screen was performed to identify drugs that were already in clinical use and that could increase SKPs activity. To identify molecules (e.g., small molecules) that promote proliferation of SKPs, a simple, reproducible and robust assay that measures cell proliferation using Alamar Blue® dye, which yields a fluorescent signal in response to metabolic activity, was developed. Compounds (1 μM to 5 μM) were added in singlet to 96-well uncoated plates, 3000 early passage dissociated sphere cells were robotically seeded, and plates were incubated in basal growth medium. After 30 hours, Alamar Blue was added and its reduction assessed after another 24 hours. Typically, there is an 8-10 fold difference in Alamar Blue reduction between positive and negative controls. A compound was identified as a hit if Alamar Blue reduction is increased by three standard deviations from the mean of all the compounds in a particular screen. In this assay, the variability of signals are low, with CV values ranging from 3.5-4.5% and the dimensionless statistical parameters Z' and Z factors >0.5, indicative of an excellent assay, as previously reported in Smith et al., EMBO Mol Med. 2:371-384, 2010. The chemical libraries used included the LOPAC 1280 collection, which includes 1280 unique low-molecular weight compounds, and the NIH collection library, which includes 446 compounds already in clinical use. Using this screen, several compounds were identified that increased SKPs sphere number in both rodent and human cell cultures, shown in Table 1 below.

TABLE 1

Compounds identified in screening assays

| Kaempferol (Kae) | MG 624 (MG) | Pramoxine (Pram) |
| Alprostadil (Alp) | Trimebutine maleate (TM) | |

Figure 1F:
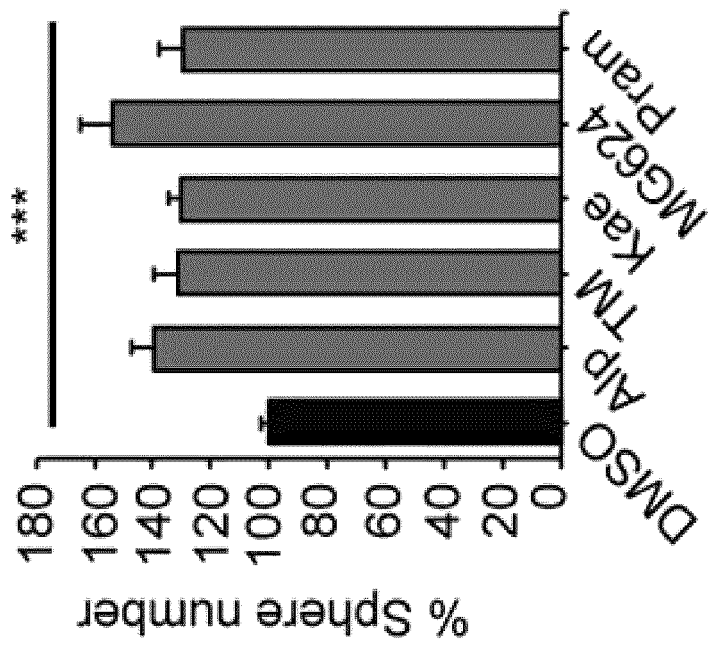
FIG. 1F is a graph showing the increase in human SKPs sphere number after treatment with 100 nM of Alp, TM, Kae, MG624, or Pram.

The hits were then validated via secondary screens of dose response sphere forming assays both in rodent and human SKPs cultures, which confirmed alprostadil (Alp), trimebutine maleate (TM), kaempferol (Kae), MG 624 (MG), and pramoxine (FIGS. 1A-1E, respectively). In particular, alp, TM, and Kae enhanced sphere number at doses as low as 1-10 nM. A comparison showed that at 100 nM, all of the drugs promoted sphere formation to similar extents (FIG. 1F). Similar results were obtained in secondary sphere formation assays with neonatal rat SKPs (FIG. 1G).

Figure 1I:
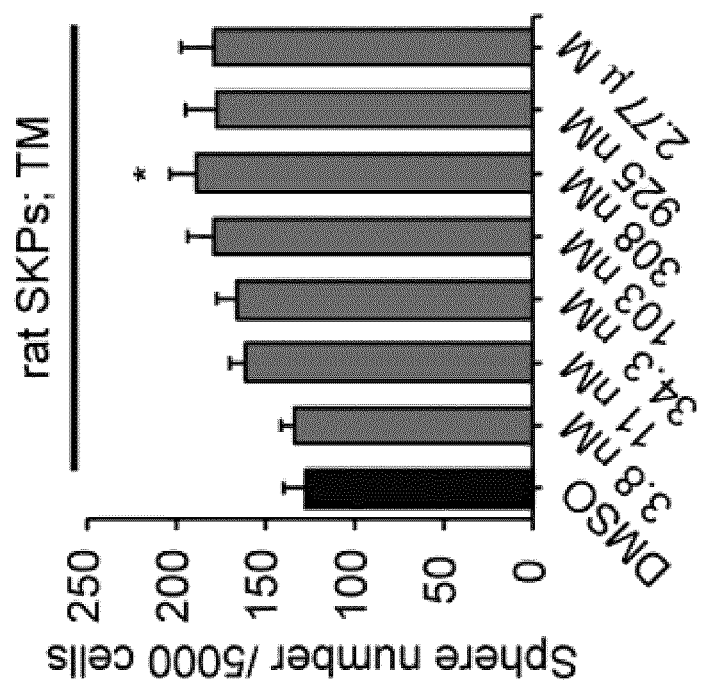
FIGS. 1H and 1I are graphs showing the dose-response curve of rat SKPs to treatment with ALP and TM, respectively.
Figure 1H:
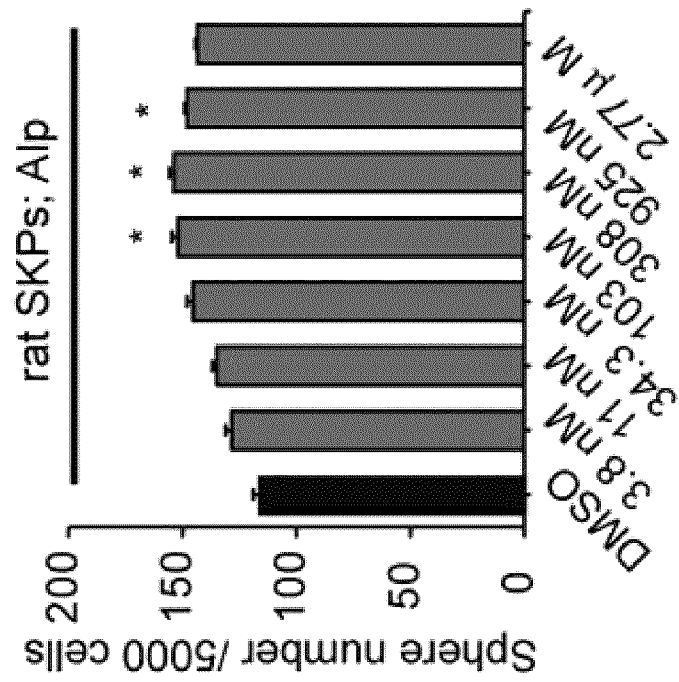
Figure 1N:
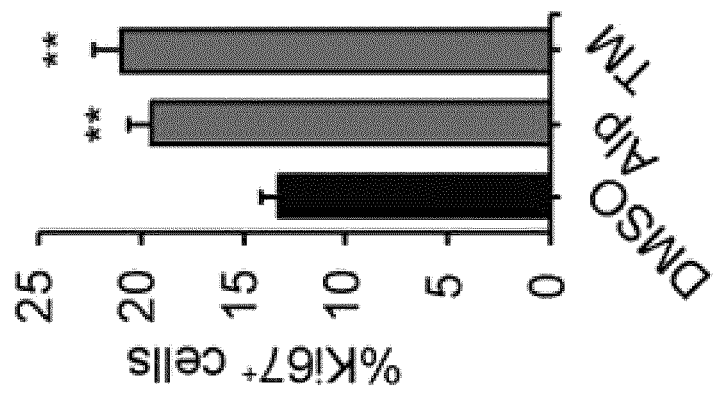
Figure 1O:
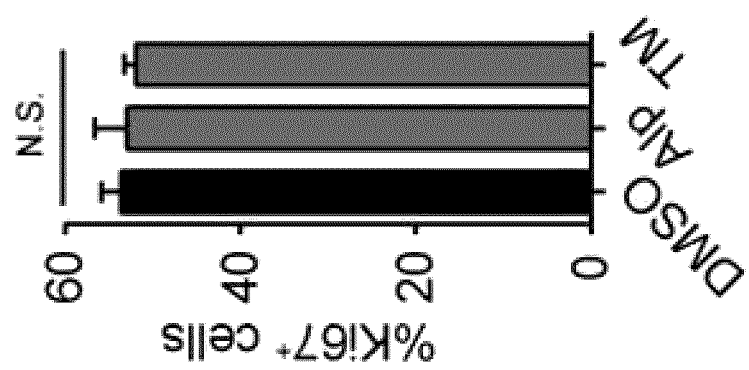

Alp and TM were further characterized by dose-response curves with rat SKPs. Sphere numbers increased in a dose-dependent fashion for both Alp and TM (FIGS. 1H-1I). A clonal density assay was also performed to validate the effect of drugs on SKPs self renewal and proliferation. As previously described in Jinno et al., Stem Cells 28:2027-2040, 2010, SKPs were dissociated and plated at 2,500 cells/mL in medium containing 1.6% methylcellulose. Cells were then treated with 100 nM of Alp, TM, Alp and TM, or DMSO and sphere formation was scored after 14 days. The data show a robust increase in sphere number and size in Alp and TM cells versus control, with no further increase when both Alp and TM were added, which suggests a similar mechanism of action for Alp and TM (FIGS. 1J-1K). For comparison, cells were also treated with latanoprost (Latan), a prostaglandin (PGF2) that is bioactive in rodent and human skin. There was a significant increase in sphere numbers after treatment Alp, TM, and Latan for 14 days (FIG. 1L). Finally, SKP proliferation was directly measured. Rat SKPs were cultured for 3-4 days, treated with Alp or TM daily for a further 2 days, and immunostained with the proliferation marker Ki67. Both Alp and TM increased Ki67-positive sphere cells by approximately 60% (FIGS. 1M-1N). These drugs are not general mitogens, since Ki67-positive NIH-3T3 cells were unaffected in similar assays (FIG. 1O). Thus, alprostadil and TM increase SKP proliferation and self-renewal.

Example 2

Assays Demonstrating the Effects of TM on Wound Healing

The effects of Alp and TM were further validated in in vivo rodent models. The model used was a Full Thickness Biopsy Punch Wound performed on the back skin of middle-aged (9 months old) C57/B16 mice (FIGS. 2A-2I). In these experiments, the hair on the back skin was shaved to expose skin and a 6 mm diameter wound was performed with a biopsy punch. Alp, TM, or vehicle were reconstituted in a composition of water-ethanol-propylene glycol (PG) and applied daily around the wound for the duration of 9 days. Topical analysis was performed to assess the degree of wound closure as well as morphometric analysis. For the analysis of wound closure, digital photographs were taken at day 0, 3, 7, and 9 post wounding. A ruler was used to calibrate the images and the wound margins were manually outlined. The wound closure rate was calculated as a percentage of the wound size on the day of surgery as previously reported in Johnston et al., Stem Cell Reports. 1(1): 38-45, 2013. Morphometric analyses of wound parameters were performed on hematoxylin and eosin-stained paraffin tissue sections from the central portion of the wound bed. Sections were scanned and images were stitched together to show the full wound bed. Morphometric analysis of different parameters was performed as described previously in Johnston et al., supra.

Figure 2A:
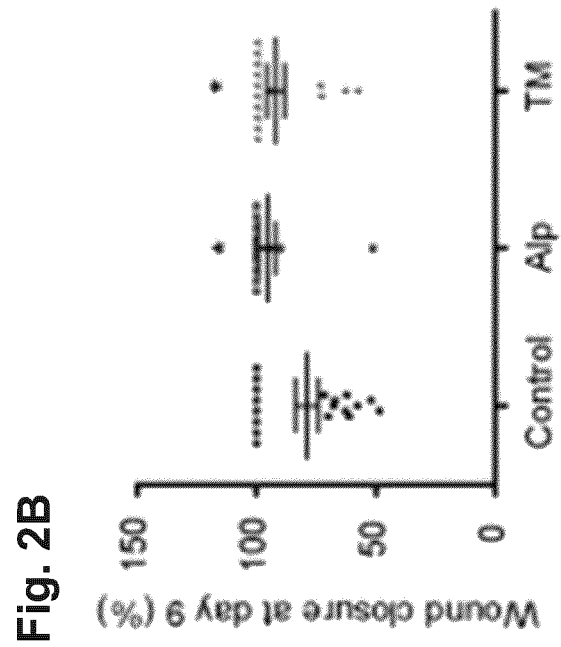
FIGS. 2A-2J show the effects of topical application of TM or Alp on wound healing in mice.
Figure 2B:
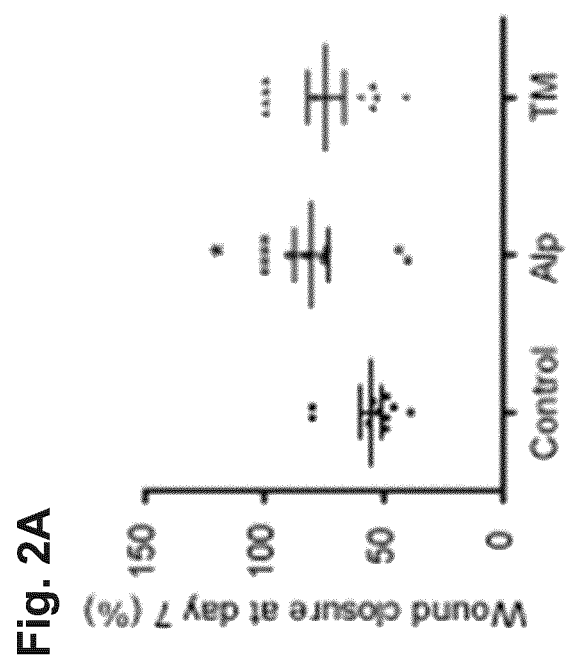
Figure 2C:
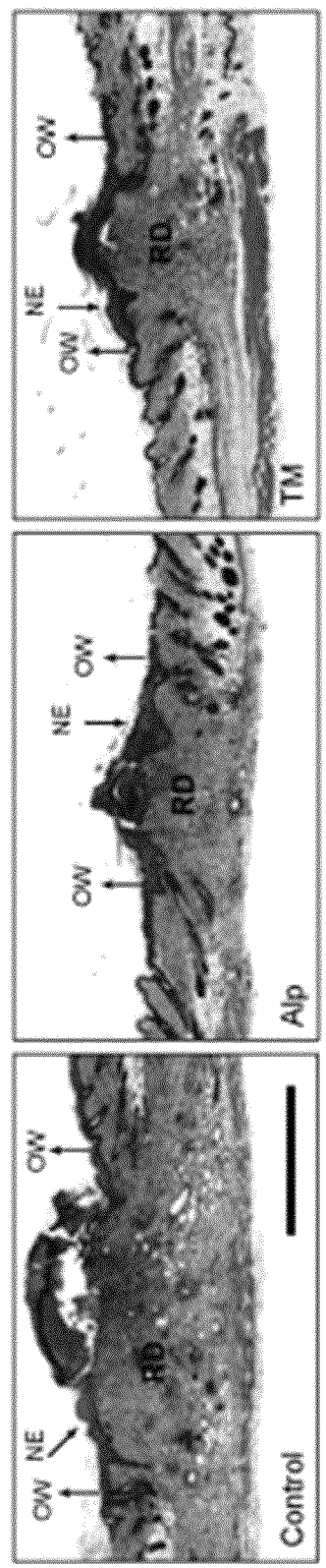
Figure 2D:
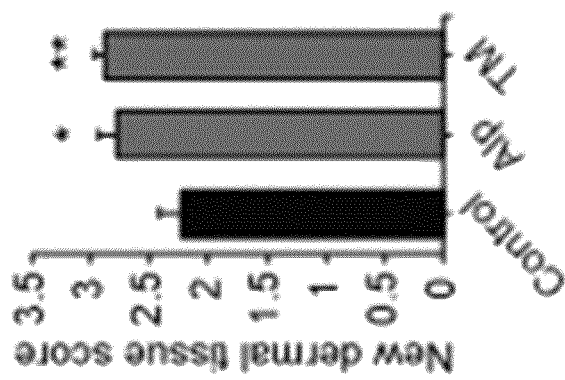
Figure 2E:
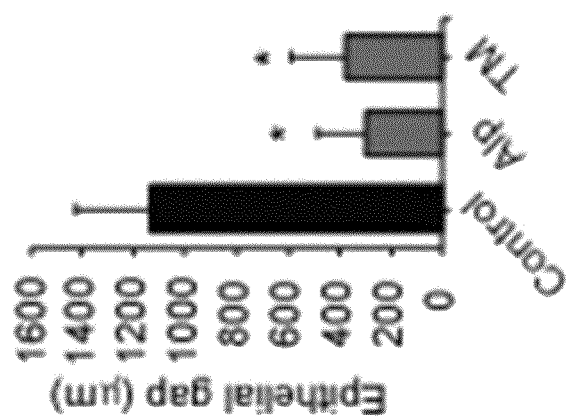
Figure 2F:
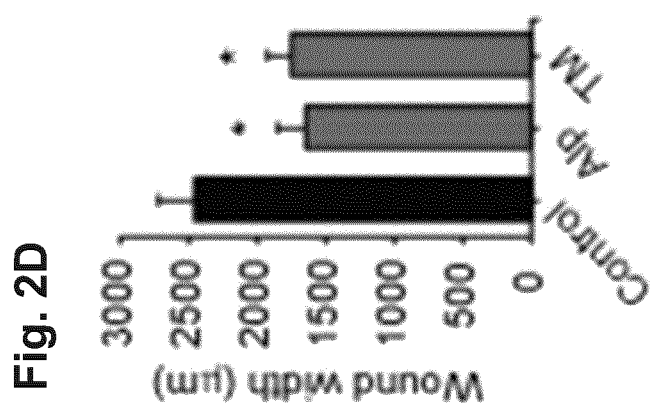
Figure 2G:
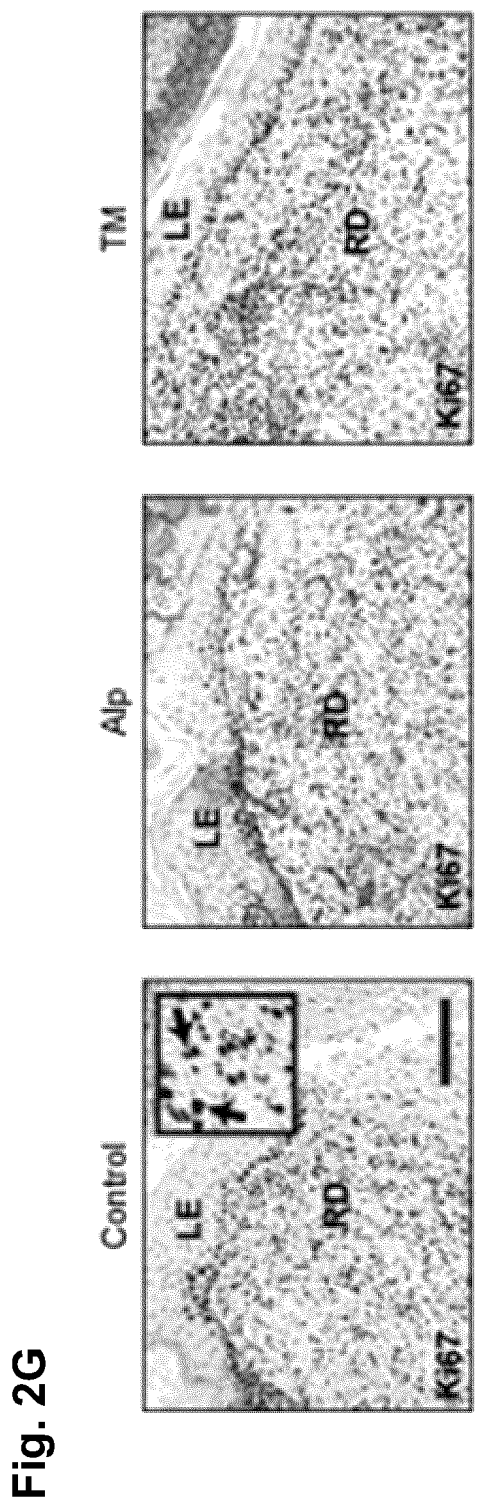
Figure 2H:
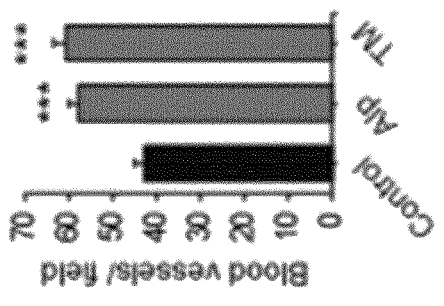
Figure 2J:
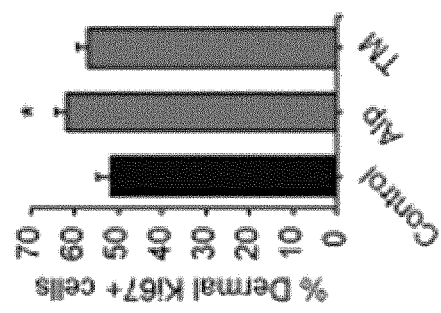
Figure 2I:
Figure 2I:
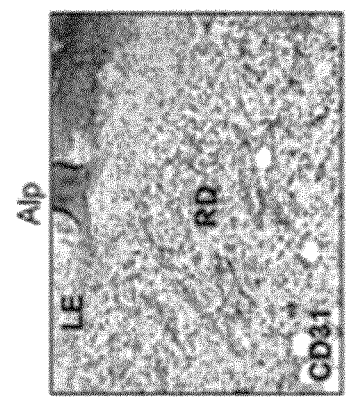
Figure 2I:
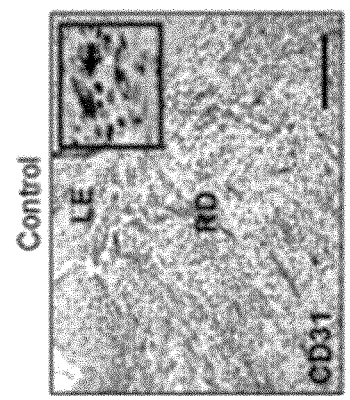

Wound healing experiments revealed that wound closure was significantly accelerated in drug-treated mice. On day 7, almost half of the Alp or TM-treated mice were fully healed, as opposed to none of the vehicle treated controls (FIG. 2A). By day 9, 70-78% of drug-treated mice were healed as compared to 44% of the vehicle-treated mice (FIG. 2B). Morphometric analyses of hematoxylin and eosin-stained paraffin sections from the central portion of the wound bed on day 9 confirmed these results (FIG. 2C). Wound width and epithelial gap were both significantly smaller in Alp or TM-treated mice (FIGS. 2D-2E). Dermal tissue regeneration was also enhanced, with a thicker layer of new dermal tissue (FIG. 2F). In alprostadil-treated mice, this coincided with increased Ki67-positive proliferating dermal cells at the leading edge of the newly formed dermis 7 days post-injury (FIGS. 2G-2H). Treatment with alprostadil or TM also increased CD31-positive blood vessels in the same region (FIGS. 2I-2J). These results demonstrate that Alp and TM promote proliferation and increase blood vessels in the wound bed.

Example 3

Assays Demonstrating the Effects of TM on Promoting Hair Growth and Dermal Maintenance To further assess the role of Alp and TM in skin maintenance and morphology, as well as hair growth, another in vivo model was used. In a hair growth assay, the back hair of young mice was depilated to induce a new hair cycle. Only those mice whose hair were in resting phase were included in the study. Drugs were applied daily on the depilated area for the duration of three weeks. Newly grown hair was collected at day 16, 19, and 21, and the length was measured. Skin samples were also collected at the end of the study to assess hair follicle density, hair cycle, and skin thickness. In the skin assays, the back hair of mice was shaved to expose skin and drugs were topically applied for the duration of one or three weeks. Skin morphology was then assessed by analyzing dermal thickness and proliferation.

Figure 3C:
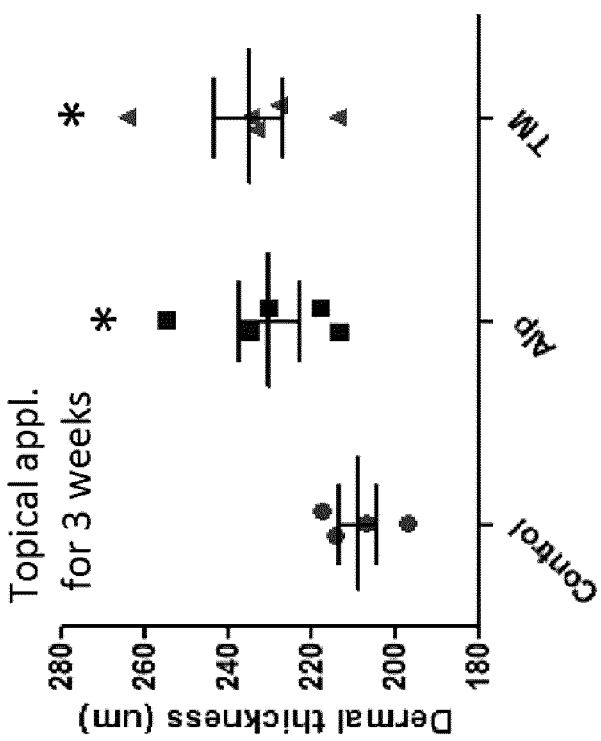
Figure 3B:
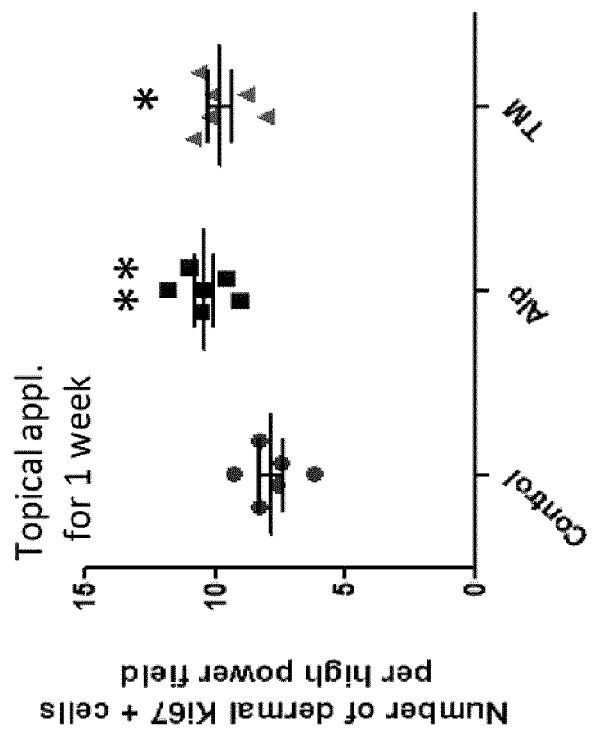
Figure 4:
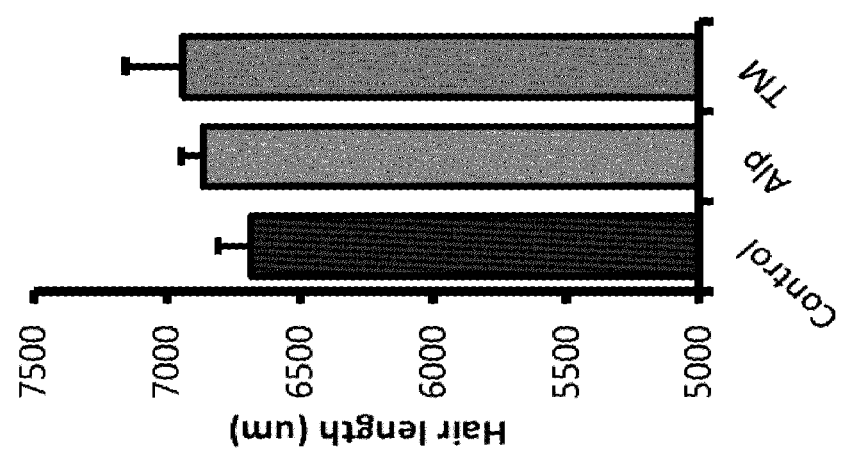
FIG. 4 shows the effects of TM and Alp on hair growth. The graph shows the hair length of Alp and TM-treated mice. n=4 mice/group.

In one week of topical treatment with TM or Alp, the number of Ki67 positive proliferating cells were increased in the dermis and within three weeks of TM or Alp treatment, an increase in dermal thickness was seen (FIGS. 3A-3C). In addition, the drug-treated mice showed a tendency to have longer hair than control. The effect on hair length was in the range of 200 μM longer than control (FIG. 4). No difference was seen in hair cycle/follicle morphology in drug-treated mice.

Example 4

Assays Demonstrating the Recruitment of Endogenous SKPs In Vivo

To assess whether the effects of topical application of Alp and TM were specific and due to recruitment of SKPs in vivo, an experiment was performed in which the drugs were applied topically for one week on the back skin of aged wounded or not wounded mice. The wound bed or control skin was dissected and SKPs were isolated and allowed to form spheres. Secondary SKP spheres were then used in a sphere forming assay. Sphere forming assays and SKPs isolation methods are previously described in Biernaskie et al., Nat. Protoc. 1:2803-2812, 2006 and Jinno et al., Stem Cells 28:2027-2040, 2010.

Figure 5:
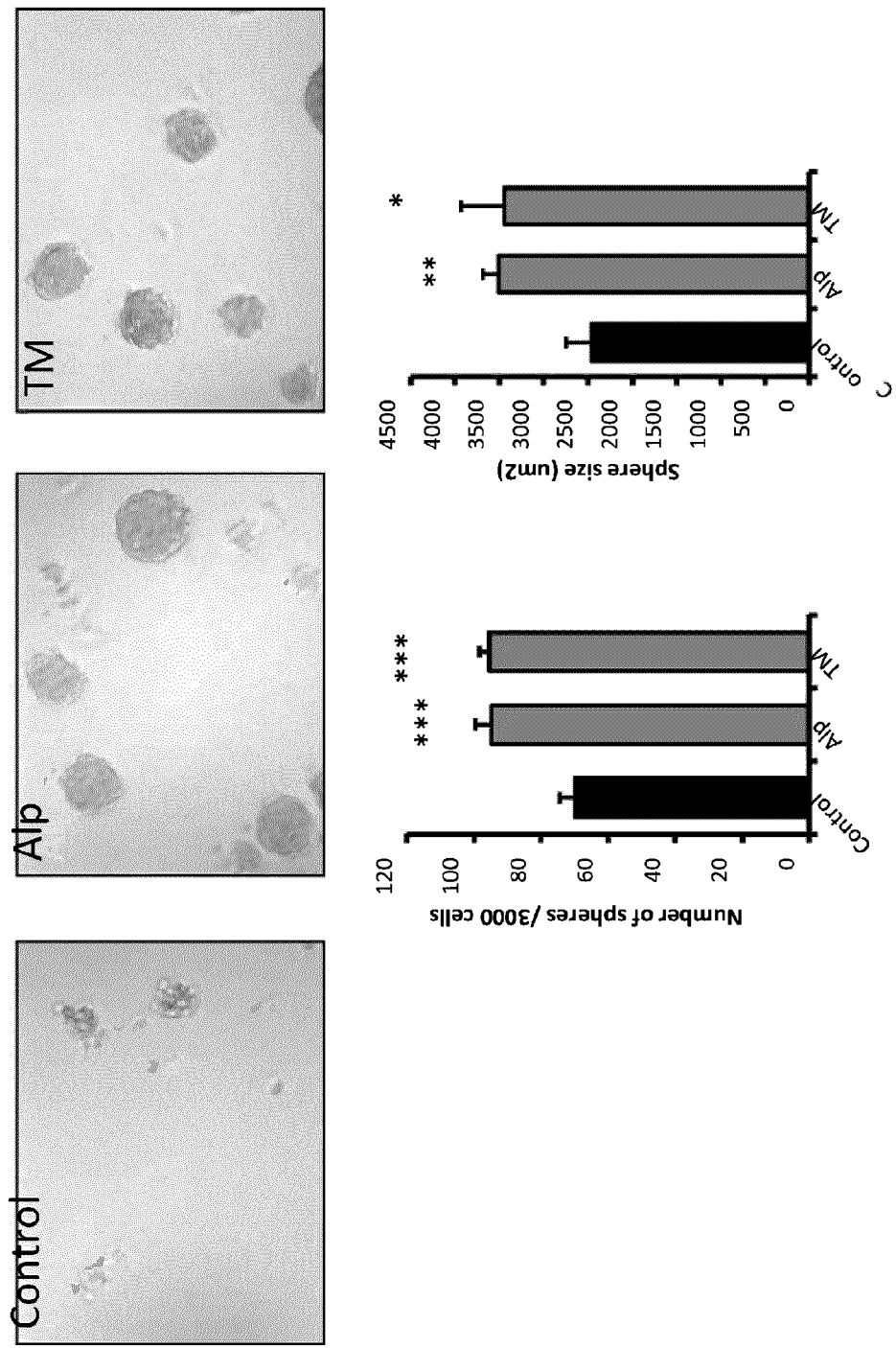
FIG. 5 shows images and graphs of the effects of TM and Alp on self-renewal and proliferation of SKPs by determining SKP sphere number in drug-treated wound beds.
Figure 6:
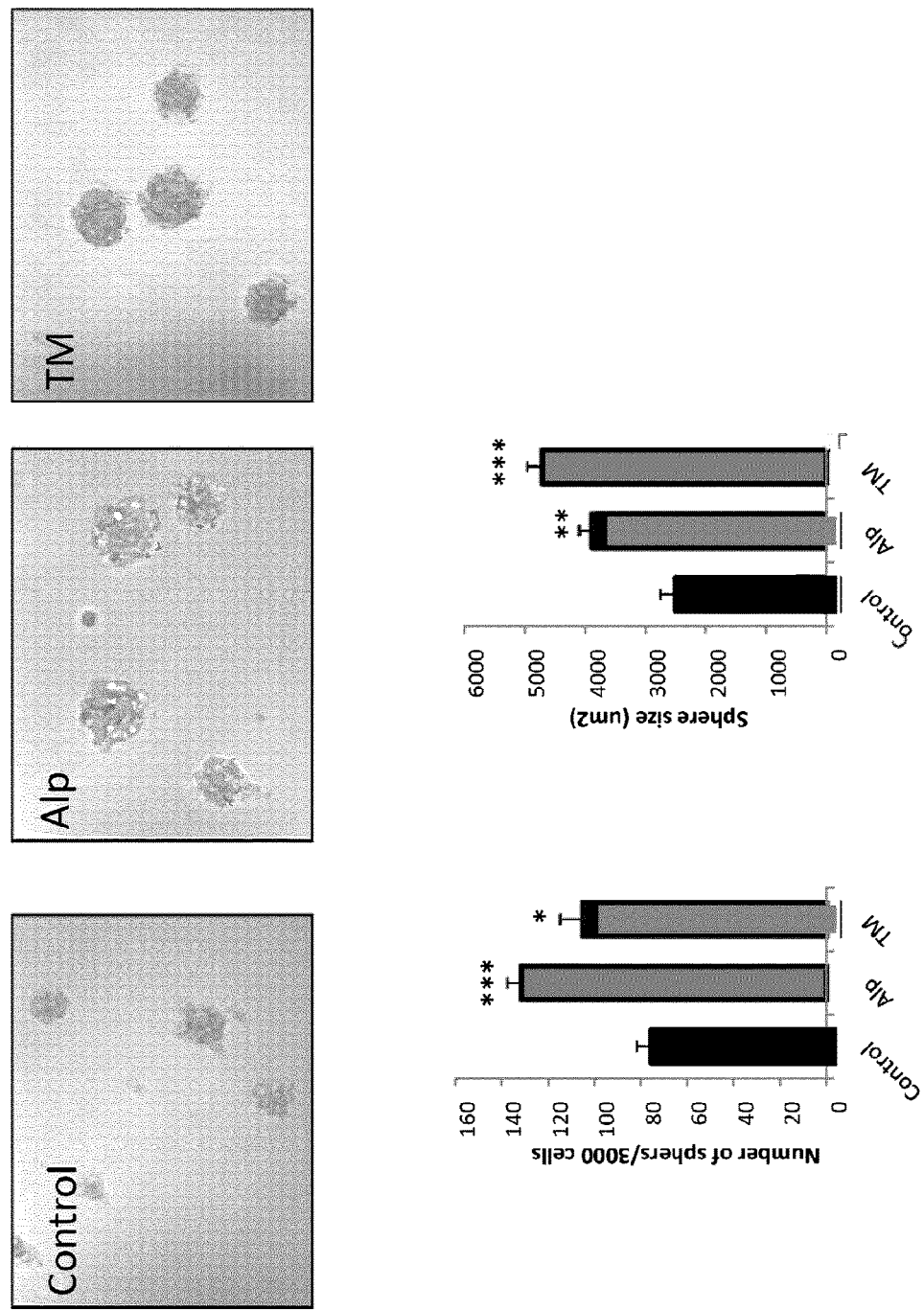
FIG. 6 shows images and graphs of the effects of TM and Alp on self-renewal and proliferation of SKPs by determining SKP sphere number in drug-treated controls.

FIGS. 5 and 6 show that SKPs derived from drug-treated wound beds (FIG. 5) or drug-treated skin (FIG. 6) were able to proliferate and self renew significantly better than control cells (without drug treatment). Together, these data suggest that in vivo topical application of Alp and TM enhance the long term self-renewal of SKPs, and thus, Alp and TM are capable of enhancing wound-healing and dermal maintenance in aged skin.

Example 5

Transcriptome Analysis of Alp and TM Long-term Enhancement of SKP Self-renewal

Figure 7A:
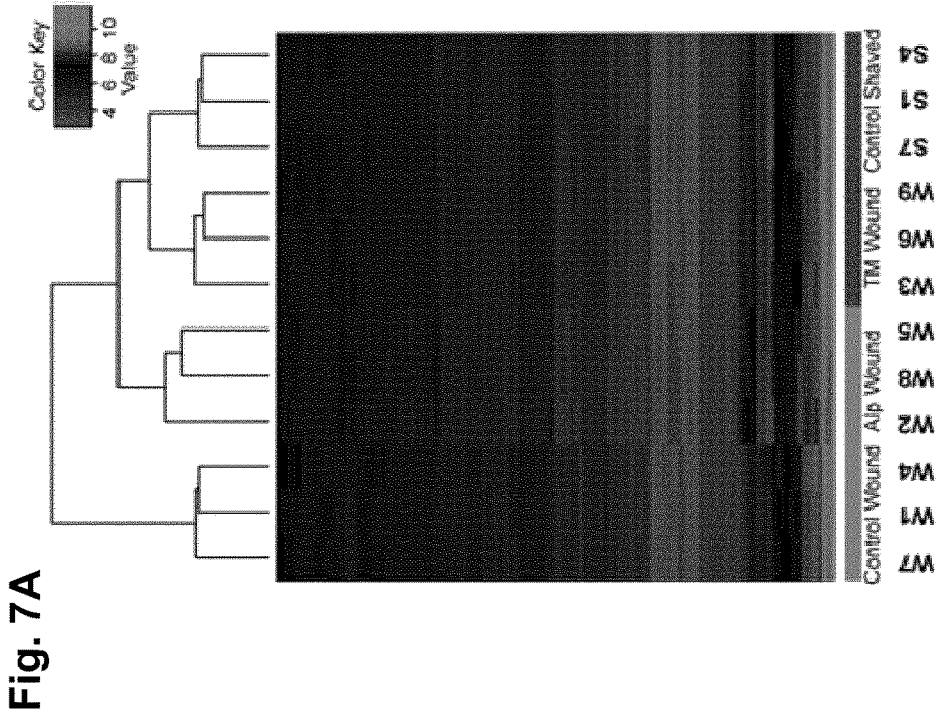
FIGS. 7A-7E show that topical treatment with TM or Alp alters self-renewal in SKPs cultured from treated skin the absence of TM or Alp and that acute TM or Alp treatment changes SKP gene expression.

To assess the long-term effects of Alp and TM treatment on the self-renewal of SKPs, transcriptome analysis was performed on the secondary SKP sphere populations described in Example 4. RNA was isolated from the SKPs cultured from drug-treated wound beds, drug-treated skin, and control skin. Transcript levels were then assessed using Affymetrix GeneChip Mouse Gene 2.0 ST Arrays for three independent biological replicates of each secondary SKP sphere population. Unbiased hierarchical clustering (using the complete-linkage method) of an Euclidean distance matrix of log 2 normalized gene expression data demonstrated that the biological replicates clustered together for each SKP treatment population. Furthermore, the clustering analysis revealed that secondary SKP populations from Alp-treated and TM-treated wounded and not wounded skin exhibited more similar transcriptomes than SKP populations isolated from control skin (FIG. 7A).

Figure 7C:
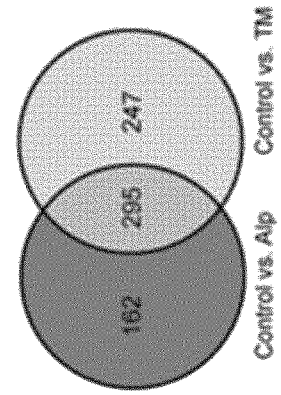
Figure 7E:
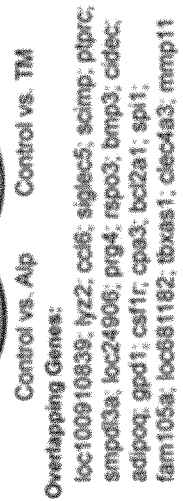
Figure 7B:
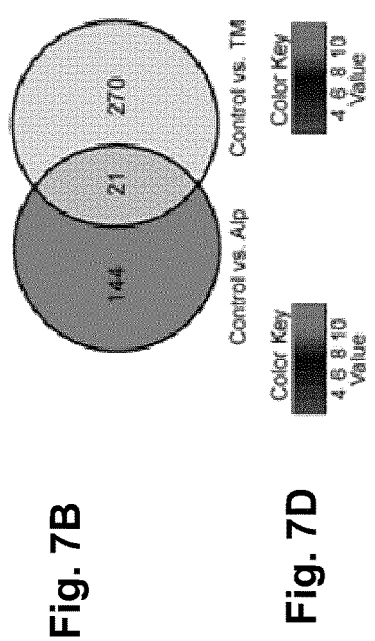

To corroborate the transcriptional similarity of the different SKP populations, differential gene expression analysis was performed using the limma bioconductor package, as described in Ritchie et al., Nucleic Acids Res. 43(7):e4, 2015. Only 165 genes and 291 genes were differentially expressed in SKPs from Alp-treated wounded skin and from TM-treated wounded skin compared to control skin, respectively ($p<0.01$ for both comparisons) (FIG. 7B). Of these differentially-expressed genes, only 21 were shared between SKPs from Alp-treated and TM-treated wounded skin. Thus, SKP populations from drug-treated wound beds or drug-treated skin are transcriptionally similar, and Alp and TM treatment enhanced the self-renewal of cultured SKP populations.

Example 6

Transcriptome Analysis of the Acute Effects of Alp and TM on SKP Self-renewal

Figure 7D:
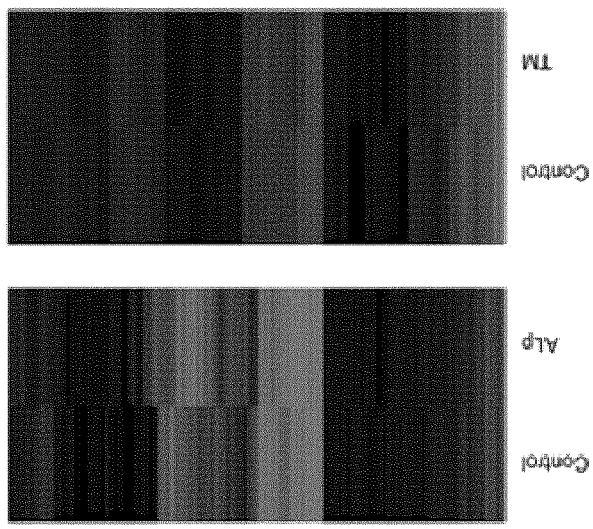

To assess the acute effects of Alp and TM, SKPs were passaged and acutely treated with Alp or TM for 24 hours, followed by microarray analysis. This analysis identified 457 and 545 differentially expressed genes in the pairwise comparisons of control skin to Alp-treated skin and control skin to TM-treated skin, respectively. More than half of the significantly different genes (295) were shared between the two groups (FIG. 7C), and the changes were generally of higher magnitude for Alp than for TM (FIG. 7D). Additionally, of the top 50 differentially expressed genes identified in the pairwise comparisons, 23 differentially expressed genes were shared between SKPs treated with Alp and TM (FIG. 7E). These results indicate a mechanistic convergence underlying the proliferation of SKPs treated with Alp and TM.

Gene ontology (GO) enrichment analysis was then performed using the GOstats bioconductor package, as described in Falcon and Genleman, Bioinforma. Oxf. Engl. 23: 257-258, 2007. Consistent with the biological effects of Alp and TM, genes associated with cell proliferation were significantly enriched for both Alp and TM, as shown in Table 2 below. In particular, genes of the MAP kinase pathway were highly enriched for both Alp and TM, indicating that activation of this pathway may play a role in self-renewal of SKPs, as shown in the Table 3 below.

TABLE 2

Enriched genes associated with cell proliferation after treatment with Alp and TM

| GO ID (Biological Process) | Ctrl. Vs. Alp (P-value) | Ctrl. Vs. TM (P-value) | Term Description |
| --- | --- | --- | --- |
| GO: 0008283 | 3.29E-11 | 3.60E-10 | Cell proliferation |
| GO: 0008284 | 1.14E-10 | 1.13E-07 | Positive regulation of cell proliferation |
| GO: 0042127 | 2.54E-10 | 1.82E-09 | Regulation of cell proliferation |

TABLE 3

Enriched genes of the MAP kinase pathway after treatment with Alp and TM

| GO ID (Biological Process) | Ctrl. Vs. Alp (P-value) | Ctrl. Vs. TM (P-value) | Term Description |
| --- | --- | --- | --- |
| GO: 0000165 | 5.12E-08 | 6.94E-05 | MAPK cascade |
| GO: 0043410 | 7.29E-08 | 0.000264 | Positive regulation of MAPK cascade |
| GO: 0043408 | 9.80E-08 | 0.000112 | Regulation of MAPK cascade |
| GO: 0070371 | 1.16E-07 | 1.76E-05 | ERK1 and ERK2 cascade |
| GO: 0070372 | 1.62E-07 | 2.34E-05 | Regulation of ERK1 and ERK2 cascade |
| GO: 0043405 | 1.86E-06 | 0.000167 | Regulation of MAPK kinase activity |
| GO: 0070374 | 3.07E-05 | 0.000504 | Positive regulation of ERK1 and ERK2 cascade |

Example 7

Alp and TM Activate the MEK-ERK Self-renewal Pathway in SKPs

Figure 8B:
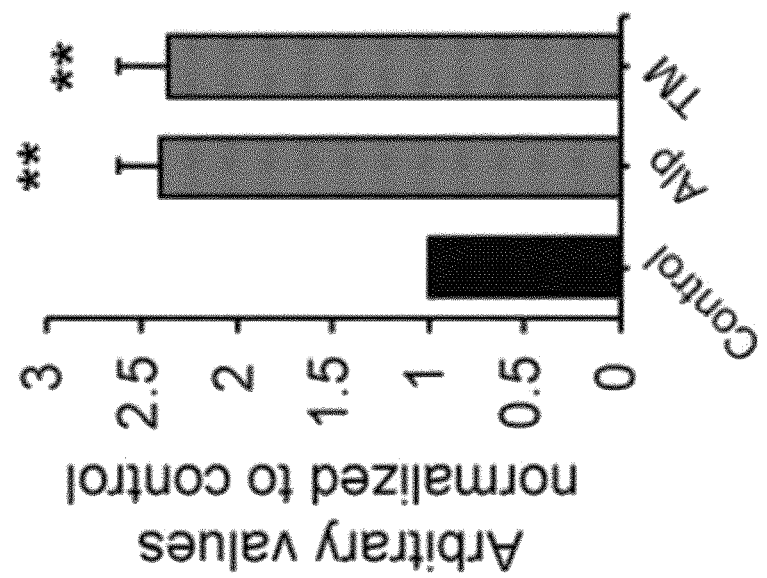
FIGS. 8A-8K show that signaling via the mitogen-activated protein kinase-extracellular signal regulated kinase (MEK-ERK) pathway is necessary for SKPs self-renewal.
Figure 8A:
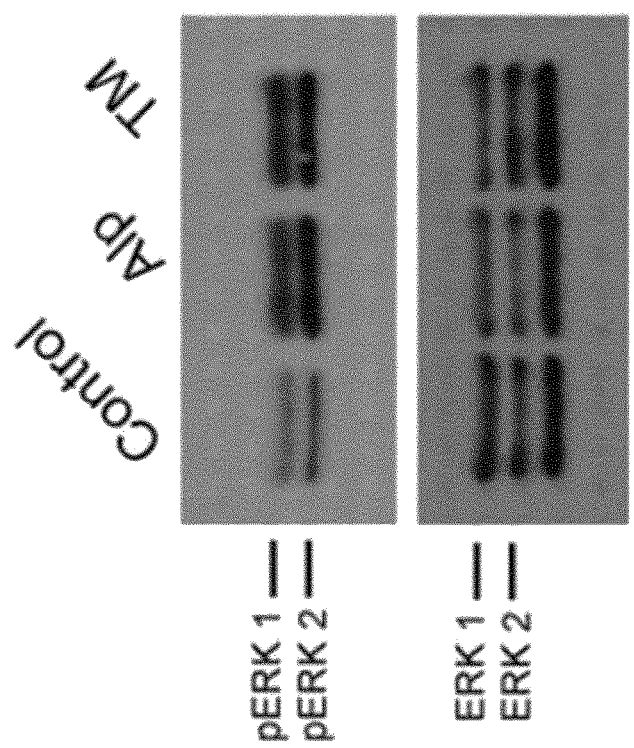
Figure 8D:
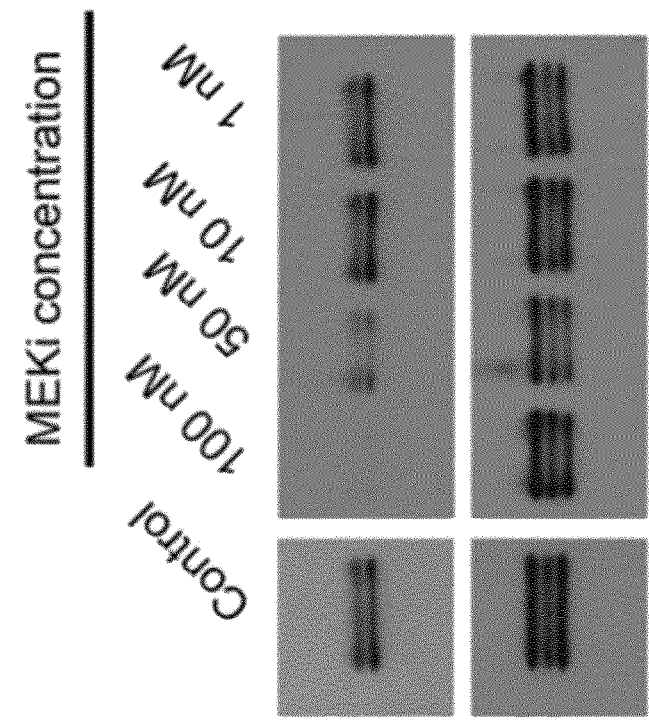
Figure 8C:
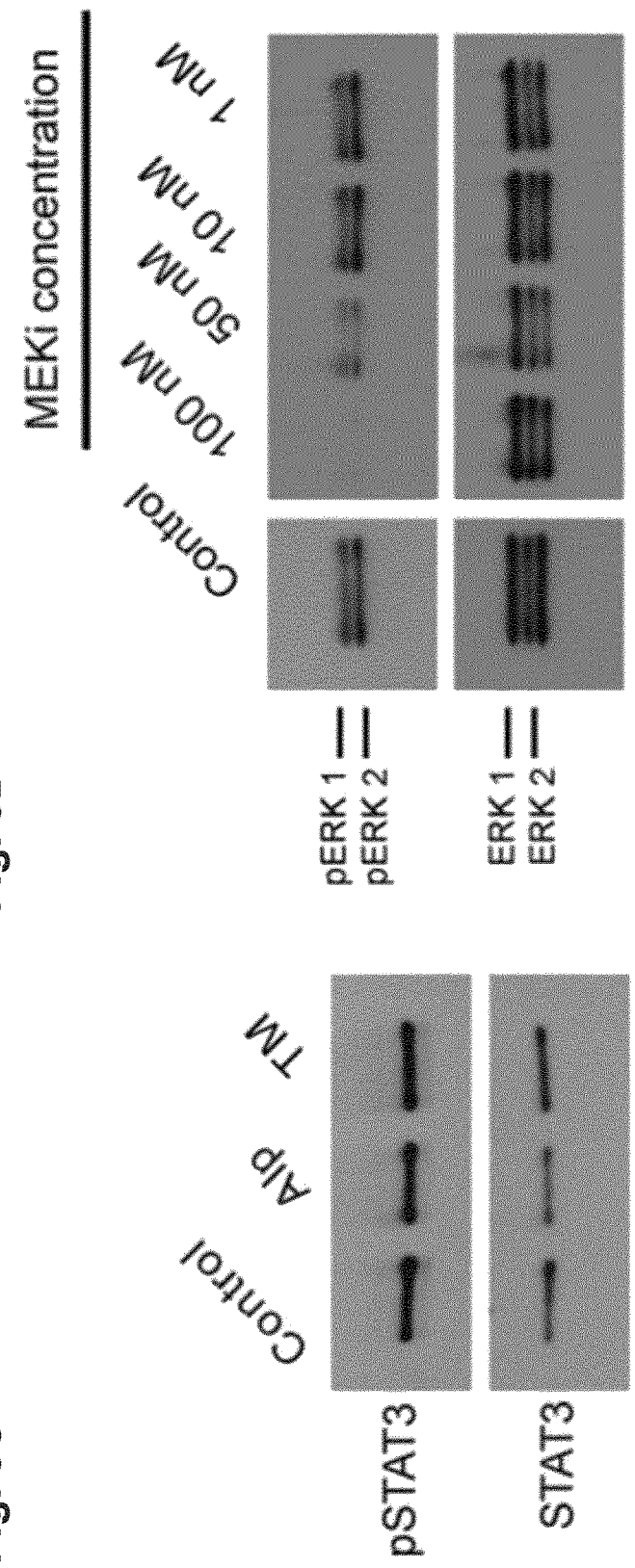

To assess whether Alp and TM activated the mitogen-activated protein kinase-extracellular signal regulated kinase (MEK-ERK) pathway in SKPs, dissociated SKPs were cultured for 24 hours and 100 nM Alp or TM was added to the SKP cultures followed by western blot analysis targeting phosphorylated, activated ERK1/2. SKPs cultured in FGF2 and EGF exhibited basal levels of ERK1/2 phosphorylation that increased approximately two-fold after treatment with Alp or TM (FIGS. 8A and 8B). In contrast, neither Alp nor TM increased the phosphorylated, activated forms of STAT3, GSK3beta, Akt1, or CREB compared to control (FIG. 8C).

Figure 8E:
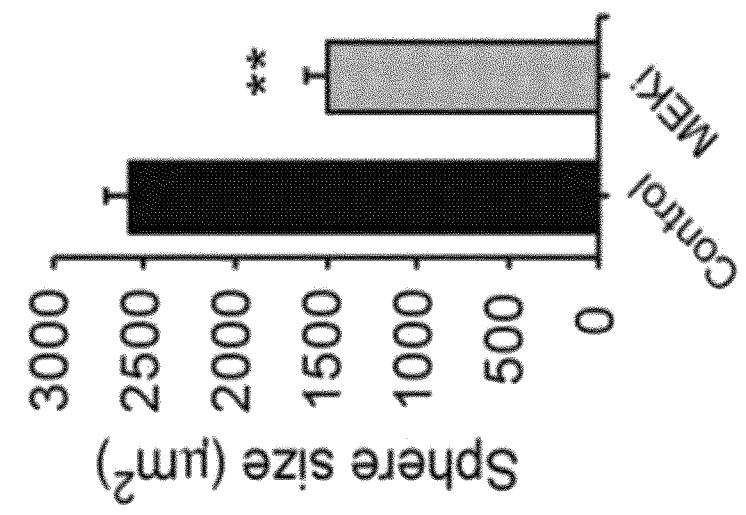
Figure 8F:
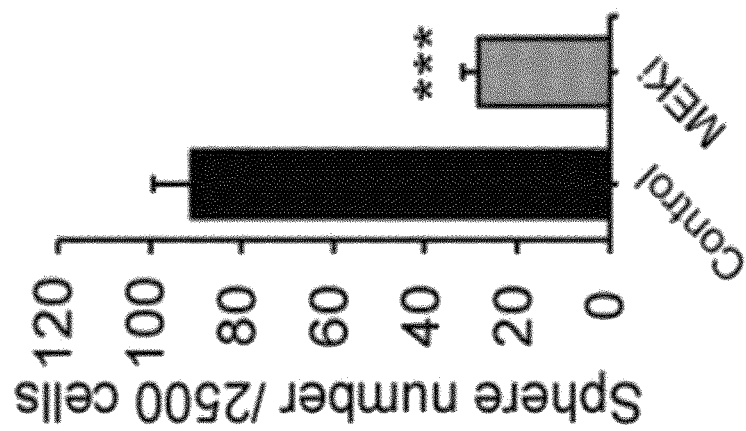
Figure 8G:
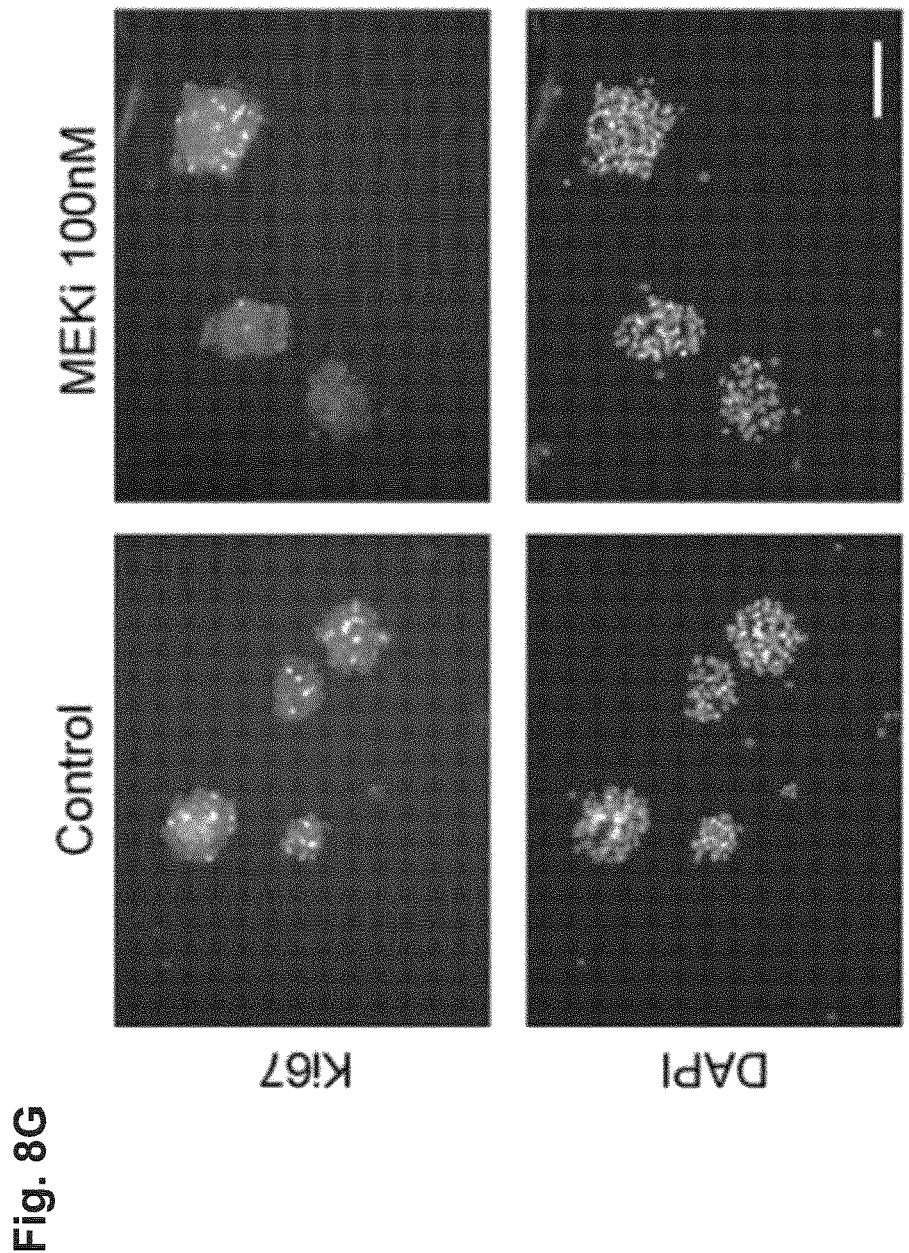
Figures 8H, 8I:
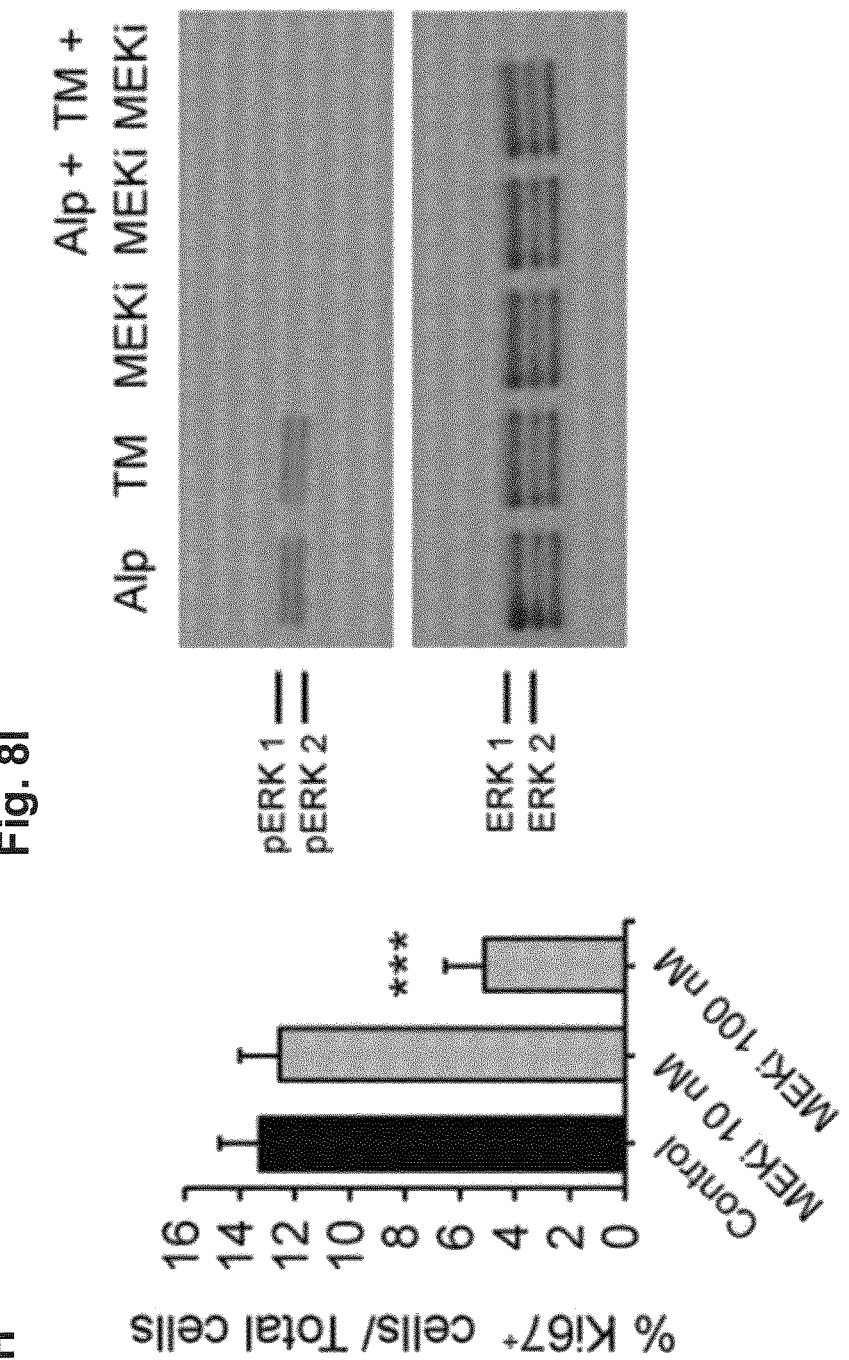

To assess whether MEK-ERK activity was important for SKPs self-renewal, the highly selective MEK1/2 inhibitor trametinib (GSK1120212) was used as described in Gilmartin et al., Clin. Cancer Res. 17: 989-1000, 2011. Trametinib was first shown to inhibit basal ERK1/2 phosphorylation in cultured SKPs (FIG. 8D). A methylcellulose colony formation assay was then used to determine the importance of MEK-ERK activity for SKPs self-renewal, and trametinib was shown to decrease both the number and size of clonal spheres grown in FGF2 and EGF (FIGS. 8E and 8F). MEK inhibition also decreased SKPs proliferation, but not survival, as monitored by Ki67 immunostaining of SKP spheres cultured for 48 hours with or without trametinib (FIGS. 8G-8H).

Figure 8K:
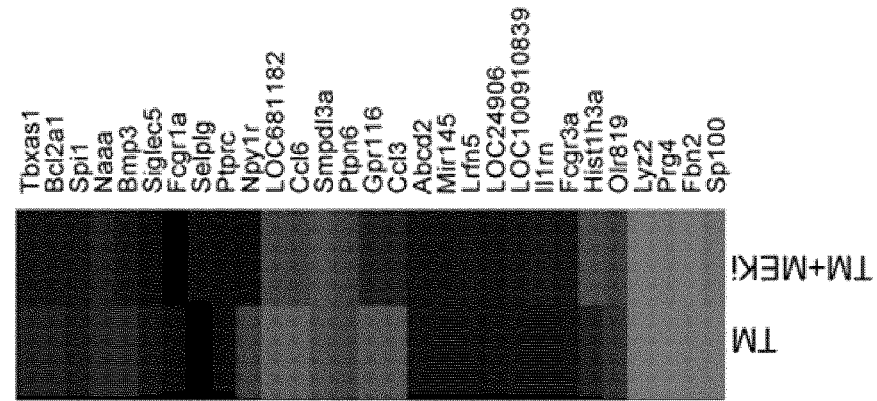
Figure 8J:
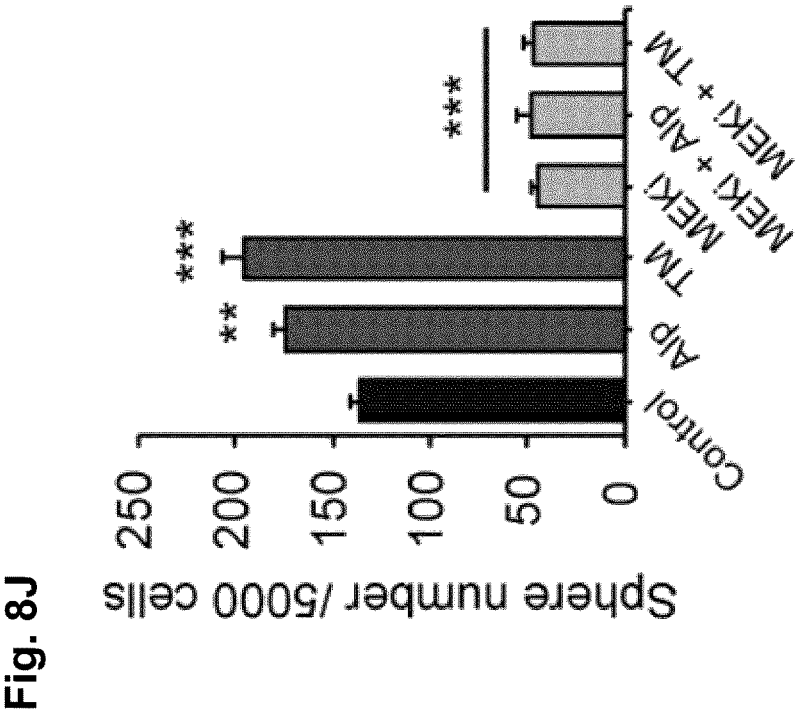

Three separate lines of evidence indicated that MEK-ERK activity was also important for drug-induced self-renewal. First, trametinib suppressed the ability of Alp and TM to increase ERK1/2 phosphorylation in SKPs cultured for 24 hours (FIG. 8I). Second, inhibition of MEK with 100 nM trametinib in 7 day sphere assays resulted in a robust decrease in sphere number, and neither TM nor Alp compensated for this decrease (FIG. 8J). Third, microarrays revealed that trametinib decreased, in part, the downstream changes in gene expression when SKPs were cultured in TM for 24 hours. Specifically, 29 of the top 50 genes changed by TM treatment exhibited a reduced fold change when trametinib was also included in the cultures (FIG. 8K).

Other Embodiments

It is noted that the foregoing has outlined some of the more pertinent non-limiting embodiments. These non-limiting embodiments may be used for many applications. Thus, although the description is made for particular arrangements and methods, the intent and concept of these non-limiting embodiments may be suitable and applicable to other arrangements and applications. It will be clear to those skilled in the art that modifications to the disclosed non-limiting embodiments can be effected. The described non-limiting embodiments ought to be construed to be merely illustrative of some of the more prominent features and applications thereof. Other beneficial results can be realized by applying these non-limiting embodiments in a different manner or modifying them in ways known to those familiar with the art. This includes the mixing and matching of features, elements and/or functions between various non-limiting embodiments is expressly contemplated herein, unless described otherwise, above.

All publications, patent applications, and patents mentioned in this specification are herein incorporated by reference to the same extent as if each independent publication, patent application, or patent was specifically and individually indicated to be incorporated by reference.

The invention claimed is:

1. A method of promoting skin repair or wound healing comprising administering to a subject in need thereof a composition comprising an effective amount of trimebutine or a pharmaceutically acceptable salt or active metabolite thereof.

2. The method of claim 1, wherein the trimebutine is trimebutine maleate or N-desmethyl trimebutine.

3. The method of claim 1, wherein the subject has a burn or an ulcer, has or previously had an infection resulting in skin loss, has undergone a surgical procedure requiring skin repair, or has an injury resulting in skin loss.

4. The method of claim 1, wherein the composition is administered until the wound substantially heals.

5. A method of promoting hair growth or treating a condition associated with hair loss comprising administering to a subject in need thereof a composition comprising an effective amount of trimebutine or a pharmaceutically acceptable salt or active metabolite thereof.

6. The method of claim 5, wherein the trimebutine is trimebutine maleate or N-desmethyl trimebutine.

7. The method of claim 5, wherein the condition associated with hair loss is selected from the group consisting of: androgenic alopecia, alopecia areata, anagen effluvium, self-induced hair loss, telogen effluvium, scarring alopecia, hair loss as a result of chemotherapy or radiation treatment, supplementing hair transplant, priming skull, and hair loss as a result of exposure to toxic chemicals.

8. The method of claim 5, wherein the compositions is administered until a symptom of hair loss improves.

9. The method of claim 5, wherein the method further comprises monitoring whether the subject experiences an improvement in hair growth.

10. The method of 1, wherein the composition is administered with a second agent.

11. The method of claim 1, wherein the composition is formulated for topical administration.

12. The method of claim 11, wherein the composition comprises from about 2% (v/v) to about 20% (v/v) of trimebutine maleate.

13. The method of claim 1, wherein the composition is formulated for oral administration.

14. The method of claim 13, wherein the composition comprises from about 5 mg to about 100 mg of trimebutine maleate.

* * * * *

UNITED STATES PATENT AND TRADEMARK OFFICE
CERTIFICATE OF CORRECTION

PATENT NO. : 9,962,360 B2
APPLICATION NO. : 15/513877
DATED : May 8, 2018
INVENTOR(S) : Freda D. Miller et al.

Page 1 of 1

It is certified that error appears in the above-identified patent and that said Letters Patent is hereby corrected as shown below:

In the Claims

Column 26, Line 45, in Claim 10, replace "The method of 1" with --The method of claim 1--.

Signed and Sealed this
Twenty-third Day of October, 2018

Andrei Iancu
*Director of the United States Patent and Trademark Office*